(12) United States Patent
Aloise et al.

(10) Patent No.: US 10,543,060 B2
(45) Date of Patent: Jan. 28, 2020

(54) FLUTED ENDODONTIC FILE

(71) Applicant: Ormco Corporation, Orange, CA (US)

(72) Inventors: Carlos A. Aloise, Rancho Cucamonga, CA (US); L. Stephen Buchanan, Santa Barbara, CA (US); Sorin Vasile Cora, Orange, CA (US); Emanuele Maretto, Orange, CA (US); Gopikrishnan Soundararajan, Santa Clara, CA (US)

(73) Assignee: Ormco Corporation, Orange, CA (US)

( * ) Notice: Subject to any disclaimer, the term of this patent is extended or adjusted under 35 U.S.C. 154(b) by 143 days.

(21) Appl. No.: 15/367,376

(22) Filed: Dec. 2, 2016

(65) Prior Publication Data

US 2017/0156818 A1 Jun. 8, 2017

Related U.S. Application Data

(60) Provisional application No. 62/277,473, filed on Jan. 11, 2016, provisional application No. 62/262,899, filed on Dec. 3, 2015.

(51) Int. Cl.
*A61C 5/42* (2017.01)

(52) U.S. Cl.
CPC ..................... *A61C 5/42* (2017.02)

(58) Field of Classification Search
CPC .............. A61C 5/023; A61C 5/40; A61C 5/42
USPC ......................................................... 433/102
See application file for complete search history.

(56) References Cited

U.S. PATENT DOCUMENTS

| | | | |
|---|---|---|---|
| 1,022,838 A * | 4/1912 | Funk | A61C 5/42 433/102 |
| 2,234,330 A | 3/1941 | Zetzsche et al. | |
| 4,396,069 A | 8/1983 | Ferber et al. | |
| 4,457,710 A | 7/1984 | McSpadden | |
| 4,605,025 A | 8/1986 | McSpadden | |
| 4,889,487 A | 12/1989 | Lovaas | |
| 4,904,185 A * | 2/1990 | McSpadden | A61C 5/42 433/102 |
| 5,035,617 A | 7/1991 | McSpadden | |
| 5,051,093 A | 9/1991 | Fitzmorris | |
| 5,067,900 A | 11/1991 | McSpadden | |
| 5,083,923 A | 1/1992 | McSpadden | |
| 5,104,316 A | 4/1992 | McSpadden | |

(Continued)

FOREIGN PATENT DOCUMENTS

| | | |
|---|---|---|
| AT | 503433 | 10/2007 |
| AU | 2009291863 | 3/2010 |

(Continued)

OTHER PUBLICATIONS

Dr. Mohammed Alshehri, "Medical Endodontic Instrumentation," http://www.endoexperience.com/documents/RotationReciprocationorcombination.pdf, Available as of Oct. 21, 2012.

(Continued)

*Primary Examiner* — Ralph A Lewis
(74) *Attorney, Agent, or Firm* — Weiss & Arons LLP

(57) ABSTRACT

Apparatus and methods for a fluted endodontic file are provided. The apparatus may include a fluted endodontic file defining a central longitudinal axis. The fluted endodontic file may include a working length extending along the central longitudinal axis. The working length may include a single flute. The working length may define an off-center cross-section having three vertices.

16 Claims, 31 Drawing Sheets

(56) References Cited

U.S. PATENT DOCUMENTS

| | | | |
|---|---|---|---|
| 5,275,562 | A | 1/1994 | McSpadden |
| 5,380,200 | A | 1/1995 | Heath et al. |
| 5,382,161 | A | 1/1995 | Roane |
| 5,421,727 | A | 6/1995 | Stevens et al. |
| RE35,070 | E | 10/1995 | Fitzmorris |
| 5,464,362 | A | 11/1995 | Heath et al. |
| RE35,147 | E | 1/1996 | Apap et al. |
| 5,498,158 | A | 3/1996 | Wong |
| 5,503,554 | A | 4/1996 | Schoeffel |
| 5,503,559 | A | 4/1996 | Vari |
| 5,503,562 | A | 4/1996 | Mays |
| 5,527,205 | A | 6/1996 | Heath et al. |
| 5,540,766 | A | 7/1996 | Castellani |
| 5,575,657 | A | 11/1996 | Welch |
| 5,586,886 | A | 12/1996 | Roane |
| 5,588,835 | A | 12/1996 | Kert |
| 5,595,486 | A | 1/1997 | Manocha |
| 5,605,460 | A | 2/1997 | Heath et al. |
| 5,628,674 | A | 5/1997 | Heath et al. |
| 5,639,239 | A | 6/1997 | Earle |
| 5,642,998 | A | 7/1997 | Riitano |
| 5,653,590 | A | 8/1997 | Heath et al. |
| 5,655,950 | A | 8/1997 | Heath et al. |
| 5,658,145 | A | 8/1997 | Maillefer et al. |
| 5,658,149 | A | 8/1997 | Munce |
| 5,713,736 | A | 2/1998 | Heath et al. |
| 5,735,689 | A | 4/1998 | McSpadden |
| 5,746,597 | A | 5/1998 | Maillefer et al. |
| 5,752,825 | A | 5/1998 | Buchanan |
| 5,759,159 | A | 6/1998 | Masreliez |
| 5,762,497 | A | 6/1998 | Heath |
| 5,762,541 | A | 6/1998 | Heath et al. |
| 5,775,903 | A | 7/1998 | Atkins |
| 5,775,904 | A | 7/1998 | Riitano |
| 5,797,747 | A | 8/1998 | Badoz et al. |
| 5,800,165 | A | 9/1998 | Kirsch et al. |
| 5,807,106 | A | 9/1998 | Heath |
| 5,833,457 | A | 11/1998 | Johnson |
| 5,836,764 | A | 11/1998 | Buchanan |
| 5,842,861 | A | 12/1998 | Buchanan |
| 5,842,862 | A | 12/1998 | Nissan |
| 5,855,479 | A | 1/1999 | Wong et al. |
| 5,857,852 | A | 1/1999 | Garman |
| 5,879,160 | A | 3/1999 | Ruddle |
| 5,882,198 | A | 3/1999 | Taylor et al. |
| 5,897,316 | A | 4/1999 | Buchanan |
| 5,902,106 | A | 5/1999 | McSpadden |
| 5,915,964 | A | 6/1999 | Walia |
| 5,915,970 | A | 6/1999 | Sicurelli, Jr. et al. |
| 5,919,044 | A | 7/1999 | Sicurelli, Jr. et al. |
| 5,921,775 | A | 7/1999 | Buchanan |
| 5,938,440 | A * | 8/1999 | McSpadden ............ A61C 5/42 433/102 |
| 5,941,705 | A | 8/1999 | Makris et al. |
| 5,941,760 | A | 8/1999 | Heath et al. |
| 5,947,730 | A | 9/1999 | Kaldestad |
| 5,967,778 | A | 10/1999 | Riitano |
| 5,980,250 | A | 11/1999 | McSpadden |
| 5,984,679 | A | 11/1999 | Farzin-Nia et al. |
| 6,004,133 | A | 12/1999 | Harrison, III |
| 6,024,565 | A | 2/2000 | Sicurelli et al. |
| 6,028,125 | A | 2/2000 | Combe et al. |
| 6,036,490 | A | 3/2000 | Johnsen et al. |
| 6,042,376 | A | 3/2000 | Cohen et al. |
| 6,053,735 | A | 4/2000 | Buchanan |
| 6,074,209 | A | 6/2000 | Johnson |
| 6,079,979 | A | 6/2000 | Riitano |
| 6,106,296 | A | 8/2000 | Johnson |
| 6,126,521 | A | 10/2000 | Shearer et al. |
| 6,128,966 | A | 10/2000 | Usui et al. |
| 6,132,215 | A | 10/2000 | Prasad et al. |
| 6,149,501 | A | 11/2000 | Farzin-Nia et al. |
| 6,155,825 | A | 12/2000 | Fischer et al. |
| 6,155,827 | A | 12/2000 | Euvrard |
| 6,171,108 | B1 | 1/2001 | Roane |
| 6,174,165 | B1 | 1/2001 | Katsuumi et al. |
| 6,197,846 | B1 | 3/2001 | Combe et al. |
| 6,213,771 | B1 | 4/2001 | Fischer |
| 6,231,340 | B1 | 5/2001 | Kildea, Jr. |
| 6,293,795 | B1 | 9/2001 | Johnson |
| 6,299,445 | B1 | 10/2001 | Garman |
| 6,302,691 | B1 | 10/2001 | Manzoli |
| 6,312,255 | B1 | 11/2001 | Hudak |
| 6,312,261 | B1 | 11/2001 | Mays |
| 6,315,558 | B1 | 11/2001 | Farzin-Nia et al. |
| 6,331,112 | B1 | 12/2001 | Lee |
| 6,334,775 | B2 | 1/2002 | Xu et al. |
| 6,343,929 | B1 | 2/2002 | Fischer |
| 6,358,049 | B1 | 3/2002 | Cerniway |
| 6,371,763 | B1 | 4/2002 | Sicurelli, Jr. et al. |
| 6,400,801 | B1 | 6/2002 | Fischer et al. |
| 6,409,506 | B1 | 6/2002 | Graybill |
| 6,413,499 | B1 | 7/2002 | Clay |
| 6,419,488 | B1 | 7/2002 | McSpadden et al. |
| 6,422,865 | B1 | 7/2002 | Fischer |
| 6,428,317 | B1 | 8/2002 | Abel |
| 6,428,319 | B1 | 8/2002 | Lopez et al. |
| 6,431,863 | B1 | 8/2002 | Sachdeva et al. |
| 6,447,297 | B1 | 9/2002 | Lopez et al. |
| 6,464,497 | B2 | 10/2002 | Landoz |
| 6,464,498 | B1 | 10/2002 | Pond |
| 6,468,079 | B1 | 10/2002 | Fischer et al. |
| 6,494,713 | B1 | 12/2002 | Pond |
| 6,500,004 | B2 | 12/2002 | Jensen et al. |
| 6,514,076 | B1 | 2/2003 | Bleiweiss et al. |
| 6,520,773 | B1 | 2/2003 | Weber |
| 6,520,775 | B2 | 2/2003 | Lee |
| 6,575,747 | B1 | 6/2003 | Riitano et al. |
| 6,579,092 | B1 | 6/2003 | Senia et al. |
| 6,585,513 | B2 | 7/2003 | Fischer |
| 6,589,052 | B1 | 7/2003 | Wilcko |
| 6,638,064 | B1 | 10/2003 | Nance |
| 6,638,067 | B2 | 10/2003 | Fischer et al. |
| 6,644,972 | B1 | 11/2003 | Mays |
| 6,652,282 | B2 | 11/2003 | Jensen et al. |
| 6,712,610 | B2 | 3/2004 | Abdennour et al. |
| 6,712,611 | B2 | 3/2004 | Garman |
| 6,722,882 | B2 | 4/2004 | Buchanan |
| 6,746,245 | B2 | 6/2004 | Riitano et al. |
| 6,764,306 | B1 | 7/2004 | DiMarino et al. |
| 6,783,438 | B2 | 8/2004 | Aloise et al. |
| 6,877,984 | B2 | 4/2005 | Tinnin |
| 6,881,488 | B2 | 4/2005 | Giordano |
| 6,890,134 | B1 | 5/2005 | Wagner et al. |
| 6,910,887 | B2 | 6/2005 | Van Den Houdt |
| 6,924,325 | B2 | 8/2005 | Qian |
| 6,926,526 | B2 | 8/2005 | Hudak |
| 6,932,505 | B2 | 8/2005 | Yao et al. |
| 6,932,605 | B2 | 8/2005 | McLean et al. |
| 6,942,484 | B2 | 9/2005 | Scianamblo |
| 6,948,935 | B2 | 9/2005 | Nusstein |
| 6,955,536 | B1 | 10/2005 | Buchanan |
| 6,966,774 | B2 | 11/2005 | Brock et al. |
| 6,968,229 | B2 | 11/2005 | Siemons |
| 6,968,619 | B2 | 11/2005 | Lewis et al. |
| 6,986,662 | B2 | 1/2006 | Haschke |
| 6,991,457 | B2 | 1/2006 | Kazen et al. |
| 7,008,223 | B2 | 3/2006 | Deutsch |
| 7,018,205 | B2 | 3/2006 | Abel |
| RE39,174 | E | 7/2006 | Buchanan |
| 7,086,864 | B2 | 8/2006 | Lopez et al. |
| 7,090,499 | B1 | 8/2006 | Mays |
| 7,094,055 | B2 | 8/2006 | Senia et al. |
| 7,094,056 | B2 | 8/2006 | Scianamblo |
| 7,097,454 | B1 | 8/2006 | Oh |
| 7,121,827 | B2 | 10/2006 | Lampert |
| 7,147,469 | B2 | 12/2006 | Garman |
| 7,163,401 | B2 | 1/2007 | Karmaker et al. |
| 7,168,952 | B2 | 1/2007 | Karmaker et al. |
| 7,172,421 | B2 | 2/2007 | Bina et al. |
| 7,198,486 | B2 | 4/2007 | Cox |
| 7,204,874 | B2 | 4/2007 | Jia et al. |
| 7,207,111 | B2 | 4/2007 | Aloise et al. |
| 7,223,100 | B2 | 5/2007 | Brock et al. |

(56) References Cited

U.S. PATENT DOCUMENTS

| | | |
|---|---|---|
| 7,226,288 B2 | 6/2007 | Schoeffel |
| 7,232,309 B2 | 6/2007 | Tse |
| 7,238,342 B2 | 7/2007 | Torabinejad et al. |
| 7,252,508 B2 | 8/2007 | Karmaker et al. |
| 7,261,561 B2 | 8/2007 | Ruddle et al. |
| 7,261,562 B2 | 8/2007 | Wagner et al. |
| 7,261,563 B2 | 8/2007 | Haschke |
| 7,270,541 B1 | 9/2007 | Johnson |
| 7,275,932 B2 | 10/2007 | Jin et al. |
| 7,300,281 B2 * | 11/2007 | Cantatore ............... A61C 5/42 433/102 |
| 7,311,522 B2 | 12/2007 | Graybill et al. |
| 7,322,105 B2 | 1/2008 | Lewis |
| 7,331,787 B2 | 2/2008 | Abdennour et al. |
| 7,338,284 B2 | 3/2008 | Lampert |
| 7,367,804 B2 | 5/2008 | Lewis |
| 7,398,598 B2 | 7/2008 | Lewis et al. |
| 7,402,040 B2 | 7/2008 | Turri |
| 7,435,086 B2 | 10/2008 | Berutti et al. |
| 7,448,867 B2 | 11/2008 | Aloise et al. |
| 7,481,652 B2 | 1/2009 | Senia et al. |
| 7,498,367 B2 | 3/2009 | Qian |
| 7,648,599 B2 | 1/2010 | Berendt |
| 7,665,212 B2 | 2/2010 | Lewis et al. |
| 7,665,991 B1 | 2/2010 | Kert |
| 7,669,332 B2 | 3/2010 | Senia et al. |
| 7,677,296 B2 | 3/2010 | Mason |
| 7,677,892 B2 | 3/2010 | Aleksandrovskiy et al. |
| 7,682,445 B2 | 3/2010 | Hermansson et al. |
| 7,713,059 B2 | 5/2010 | Hof et al. |
| 7,731,498 B2 | 6/2010 | McSpadden |
| 7,740,480 B2 | 6/2010 | Badoz et al. |
| 7,743,505 B2 | 6/2010 | Lewis et al. |
| 7,766,657 B2 | 8/2010 | Jaunberzins |
| 7,771,198 B2 | 8/2010 | Euvrard et al. |
| 7,785,174 B2 | 8/2010 | Badoz et al. |
| 7,806,690 B2 | 10/2010 | Heath et al. |
| 7,828,550 B2 | 11/2010 | Wagner et al. |
| 7,833,015 B2 | 11/2010 | Tuttle et al. |
| 7,833,016 B2 | 11/2010 | Gharib et al. |
| 7,833,017 B2 | 11/2010 | Hof et al. |
| 7,863,349 B2 | 1/2011 | Tuttle et al. |
| 7,891,977 B2 | 2/2011 | Riva |
| 7,942,961 B2 | 5/2011 | Asgary |
| 7,946,849 B2 | 5/2011 | Abdennour et al. |
| 7,955,078 B2 | 6/2011 | Scianamblo |
| 7,959,441 B2 | 6/2011 | Glover et al. |
| 7,967,605 B2 | 6/2011 | Goodis |
| 7,977,406 B2 | 7/2011 | Hsieh et al. |
| 7,980,853 B2 | 7/2011 | Riitano |
| 8,002,544 B2 | 8/2011 | Rizoiu et al. |
| 8,043,088 B2 | 10/2011 | Johnson |
| 8,047,842 B2 | 11/2011 | Johnson |
| 8,062,033 B2 | 11/2011 | Luebke |
| 8,075,874 B2 | 12/2011 | Torabinejad et al. |
| 8,083,873 B2 | 12/2011 | Luebke |
| 8,088,838 B2 | 1/2012 | Hsieh et al. |
| 8,105,085 B1 | 1/2012 | Heath et al. |
| 8,109,763 B2 | 2/2012 | Levy et al. |
| 8,152,743 B2 | 4/2012 | Maître et al. |
| 8,182,265 B2 | 5/2012 | McSpadden |
| 8,215,955 B2 | 7/2012 | Lee |
| 8,215,960 B2 | 7/2012 | Wagner et al. |
| 8,221,117 B2 | 7/2012 | Rizoiu et al. |
| 8,230,994 B2 | 7/2012 | Johnsen et al. |
| 8,235,719 B2 | 8/2012 | Ruddle et al. |
| 8,268,278 B2 | 9/2012 | Boudeville et al. |
| 8,328,552 B2 | 12/2012 | Ruddle et al. |
| 8,348,863 B2 | 1/2013 | Gamba et al. |
| 8,388,345 B2 | 3/2013 | Ruddle |
| 8,393,899 B2 | 3/2013 | Heath et al. |
| 8,408,901 B2 | 4/2013 | Buchanan |
| 8,413,330 B2 | 4/2013 | Johnson |
| 8,439,682 B1 | 5/2013 | Heath et al. |
| 8,454,361 B2 | 6/2013 | Scianamblo |
| 8,474,635 B2 | 7/2013 | Johnson |
| 8,496,476 B2 | 7/2013 | Scianamblo |
| 8,506,293 B2 | 8/2013 | Pond |
| 8,506,985 B2 | 8/2013 | Garcia De Castro Andrews et al. |
| RE44,509 E | 9/2013 | Pond |
| 8,562,341 B2 | 10/2013 | Luebke |
| 8,568,142 B2 | 10/2013 | Rzhanov et al. |
| 8,602,779 B2 | 12/2013 | Simons |
| 8,614,263 B2 | 12/2013 | Mante et al. |
| 8,644,978 B1 | 2/2014 | Heath et al. |
| 8,647,116 B2 | 2/2014 | Becker et al. |
| 8,703,294 B2 | 4/2014 | Zhang et al. |
| RE44,917 E | 5/2014 | Tuttle et al. |
| 8,714,978 B2 | 5/2014 | Borgschulte |
| 8,727,772 B2 | 5/2014 | Jaunberzins |
| 8,727,773 B2 | 5/2014 | Luebke |
| 8,753,120 B2 | 6/2014 | Pitel |
| 8,753,121 B2 | 6/2014 | Gharib et al. |
| 8,789,444 B2 | 7/2014 | Johnson |
| 8,790,116 B2 | 7/2014 | Becker et al. |
| 8,797,991 B2 | 8/2014 | Diachina et al. |
| 8,827,705 B2 | 9/2014 | Schoeffel |
| 8,876,991 B2 | 11/2014 | Luebke |
| 8,882,504 B2 | 11/2014 | Scianamblo |
| 8,911,573 B2 | 12/2014 | Heath et al. |
| 8,926,949 B2 | 1/2015 | Dayanim |
| 8,932,055 B2 | 1/2015 | Armanino |
| 8,932,056 B2 | 1/2015 | Scianamblo |
| 8,960,576 B2 | 2/2015 | Torabinejad et al. |
| 9,000,332 B2 | 4/2015 | Brown |
| 9,005,377 B2 | 4/2015 | Heath et al. |
| 9,033,706 B2 | 5/2015 | Lee et al. |
| 9,041,323 B2 | 5/2015 | Brown et al. |
| 9,078,722 B2 | 7/2015 | Johnson |
| 9,084,651 B2 | 7/2015 | Laufer |
| 9,101,436 B2 | 8/2015 | Chow et al. |
| 9,138,299 B2 | 9/2015 | Van Lierde et al. |
| 9,351,803 B2 | 5/2016 | Scianamblo |
| 9,662,181 B2 | 5/2017 | Scianamblo |
| 9,878,366 B2 | 1/2018 | Johnson |
| 9,902,025 B2 | 2/2018 | Shotton et al. |
| 9,931,179 B2 | 4/2018 | Rouiller |
| 2002/0006599 A1 | 1/2002 | Davidson |
| 2002/0137008 A1 | 9/2002 | McSpadden et al. |
| 2003/0029474 A1 | 2/2003 | Gibbs et al. |
| 2003/0077553 A1 | 4/2003 | Brock |
| 2003/0156980 A1 | 8/2003 | Fischer et al. |
| 2004/0023186 A1 | 2/2004 | McSpadden |
| 2004/0191723 A1 | 9/2004 | Shearer et al. |
| 2004/0219484 A1 | 11/2004 | Scianamblo |
| 2004/0219485 A1 | 11/2004 | Scianamblo |
| 2005/0118550 A1 | 6/2005 | Turri |
| 2005/0266375 A1 | 12/2005 | Brock et al. |
| 2005/0287498 A1 | 12/2005 | Schoeffel |
| 2006/0068362 A1 | 3/2006 | Desrosiers et al. |
| 2006/0216668 A1 | 9/2006 | Scianamblo |
| 2006/0228668 A1 | 10/2006 | McSpadden |
| 2006/0228669 A1 | 10/2006 | Scianamblo |
| 2006/0265858 A1 | 11/2006 | McSpadden |
| 2006/0281047 A1 | 12/2006 | Badoz et al. |
| 2007/0054238 A1 | 3/2007 | Hof et al. |
| 2007/0059663 A1 | 3/2007 | Scianamblo |
| 2007/0116532 A1 | 5/2007 | Lewis |
| 2007/0178426 A1 | 8/2007 | Brock et al. |
| 2008/0153055 A1 | 6/2008 | Senia et al. |
| 2008/0213720 A1 | 9/2008 | Lewis et al. |
| 2010/0003637 A1 | 1/2010 | Johnson |
| 2010/0092922 A1 | 4/2010 | Ruddle |
| 2010/0233648 A1 | 9/2010 | McSpadden et al. |
| 2010/0255442 A1 | 10/2010 | McSpadden |
| 2011/0159458 A1 | 6/2011 | Heath et al. |
| 2011/0217673 A1 | 9/2011 | Scianamblo |
| 2011/0271529 A1 | 11/2011 | Gao et al. |
| 2012/0107766 A1 | 5/2012 | Borgschulte |
| 2012/0219927 A1 | 8/2012 | Maxwell et al. |
| 2012/0231413 A1 | 9/2012 | McSpadden et al. |
| 2013/0244200 A1 | 9/2013 | Rota et al. |
| 2013/0273497 A1 | 10/2013 | Scianamblo |
| 2013/0302749 A1 | 11/2013 | Scianamblo |

(56) References Cited

U.S. PATENT DOCUMENTS

| | | | |
|---|---|---|---|
| 2014/0004480 A1* | 1/2014 | Breguet | A61C 5/023 433/102 |
| 2014/0045142 A1 | 2/2014 | Becker et al. | |
| 2014/0315147 A1 | 10/2014 | Borgschulte | |
| 2015/0024342 A1 | 1/2015 | Jaunberzins | |
| 2015/0044631 A1 | 2/2015 | Lifshitz et al. | |
| 2015/0072307 A1 | 3/2015 | Scianamblo | |
| 2015/0125811 A1 | 5/2015 | Lifshitz et al. | |
| 2015/0164614 A1 | 6/2015 | Shotton et al. | |
| 2015/0164615 A1 | 6/2015 | Shotton et al. | |
| 2015/0164617 A1 | 6/2015 | Ammon et al. | |
| 2015/0173853 A1 | 6/2015 | Scianamblo | |
| 2015/0216624 A1 | 8/2015 | Shotton et al. | |
| 2016/0008092 A1 | 1/2016 | Heath et al. | |
| 2016/0256237 A1 | 9/2016 | Lee et al. | |
| 2017/0362694 A1 | 12/2017 | Luebke | |
| 2018/0008374 A1 | 1/2018 | Rota et al. | |
| 2018/0028280 A1 | 2/2018 | Scianamblo | |
| 2018/0036789 A1 | 2/2018 | Luebke | |
| 2018/0049845 A1 | 2/2018 | McSpadden | |
| 2018/0085195 A1 | 3/2018 | Rouiller | |
| 2018/0110588 A1 | 4/2018 | Aloise | |
| 2018/0125609 A1 | 5/2018 | Malagnino | |
| 2018/0142377 A1 | 5/2018 | Gao et al. | |
| 2018/0177568 A1 | 6/2018 | Breguet et al. | |

FOREIGN PATENT DOCUMENTS

| | | |
|---|---|---|
| CA | 2477098 | 9/2003 |
| CA | 2784175 | 3/2010 |
| CH | 704235 | 6/2012 |
| CH | 704706 | 9/2012 |
| CN | 1642493 | 7/2005 |
| CN | 1917826 A | 2/2007 |
| CN | 1964679 | 5/2007 |
| CN | 100418491 | 9/2008 |
| CN | 201453385 | 5/2010 |
| CN | 102215772 | 10/2011 |
| CN | 1917826 B | 7/2012 |
| CN | 103458818 | 12/2013 |
| CN | 103561676 | 2/2014 |
| CN | 104080420 | 10/2014 |
| CN | 104582630 | 4/2015 |
| DE | 202013006514 | 11/2013 |
| DK | DK/EP1478301 | 7/2010 |
| EP | 0522130 | 1/1993 |
| EP | 0691826 | 1/1996 |
| EP | 0902661 | 3/1999 |
| EP | 1075228 | 2/2001 |
| EP | 1196109 | 4/2002 |
| EP | 1708638 | 10/2006 |
| EP | 1709934 | 10/2006 |
| EP | 2438884 A1 | 4/2012 |
| EP | 2438884 B1 | 4/2012 |
| EP | 2699189 | 2/2014 |
| ES | 2342930 | 7/2010 |
| ES | 2363981 | 8/2011 |
| FR | 2798277 | 3/2001 |
| FR | 2971932 | 8/2012 |
| IN | 261137 | 8/2007 |
| IN | IN1222/MUMNP/2014 | 3/2015 |
| JP | 4443934 | 8/2005 |
| JP | 2005525155 | 8/2005 |
| JP | 4782698 | 7/2011 |
| JP | 4813486 | 11/2011 |
| JP | 2012501762 | 1/2012 |
| JP | 2014533557 | 12/2014 |
| JP | 5768190 | 8/2015 |
| KR | 1020110050563 | 5/2011 |
| RU | 2011113964 | 10/2012 |
| RU | 2013150909 | 10/2015 |
| WO | WO9211833 | 7/1992 |
| WO | WO9307828 | 4/1993 |
| WO | WO9314714 | 8/1993 |
| WO | WO9740771 | 11/1997 |
| WO | WO9803126 | 1/1998 |
| WO | WO0051516 | 9/2000 |
| WO | WO0103601 | 1/2001 |
| WO | WO03015652 A2 | 2/2003 |
| WO | WO03015652 A3 | 2/2003 |
| WO | WO03071978 | 9/2003 |
| WO | WO2004091422 A2 | 10/2004 |
| WO | WO2004091422 A3 | 10/2004 |
| WO | WO2004098434 | 11/2004 |
| WO | WO2004098438 | 11/2004 |
| WO | WO2005070320 | 8/2005 |
| WO | WO2005122943 A2 | 12/2005 |
| WO | WO2005122943 A3 | 12/2005 |
| WO | IN/PCT/2006/01487/MUM | 5/2007 |
| WO | IN/PCT/2006/03358/DEL | 8/2007 |
| WO | WO2010/030668 | 3/2010 |
| WO | WO2012045455 | 4/2012 |
| WO | WO2012079183 | 6/2012 |
| WO | WO2012114052 | 8/2012 |
| WO | WO2012126128 | 9/2012 |
| WO | WO2012143918 | 10/2012 |
| WO | WO2013074896 | 5/2013 |
| WO | WO2013076717 | 5/2013 |
| WO | WO2013109923 | 7/2013 |
| WO | WO2013157000 | 10/2013 |
| WO | WO2014/141241 | 9/2014 |
| WO | WO2014205411 | 12/2014 |
| WO | WO2015059707 A1 | 4/2015 |
| WO | WO2015059707 A8 | 6/2015 |
| WO | WO2015108621 | 7/2015 |
| WO | WO2018/105997 | 6/2018 |

OTHER PUBLICATIONS

"Vortex Blue Rotary Files," Dentsply Tulsa Dental Specialties, 2012.

"Surf the Canal with Confidence Wave One Gold," Dentsply Tulsa Dental Specialties, Apr. 2015.

"What is the Difference Between the Rake Angle and Cutting Angle?" http://www.endoexperience.com/filecabinet/Clinical%20Endodontics/Instruments%20-%20Files/McSpadden%20Discussions/rake%20and%20cutting%20angle.pdf, Retrieved on Dec. 5, 2016.

European Patent Office Extended Search Report in European Patent Application No. 16202063.0, dated May 16, 2017.

European Patent Office Examination Report in European Patent Application No. 16202063.0, dated Apr. 23, 2018.

Y. Yahata et al, International Endodontic Journal 42, 621-626: "Effect of Heat Treatment on Transformation Temperatures and Bending Properties of Nickel-Titanium Endodontic Instruments," Jun. 1, 2009.

International Search Report in Application No. PCT/US2017/025854, dated Jul. 31, 2017.

Written Opinion in Application No. PCT/US2017/025854, dated Jul. 31, 2017.

Extended European Search Report in Application No. 17197635.0, dated Jun. 13, 2018.

Carrotte, P., "Endodontics: Part 5 Basic Instruments and Materials for Root Canal Treatment," https://www.nature.com/articles/4811738, British Dental Journal, vol. 197, No. 8, Oct. 23, 2004.

Ruddle, Clifford J., "Endodontic Canal Preparation WaveOne Single-File Technique," https://www.endoruddle.com/tc2pdfs/126/WaveOne_Jan2012.pdf, Dentistry Today, Jan. 2012.

"Instruments Used in Endodontics," Retrieved on Sep. 5, 2017.

Dr. Barbara Muller, "A Short History of the NiTi File Revolution," https://www.dental-tribune.com/clinical/a-short-history-of-the-niti-file-revolution/, May 24, 2016.

Examination Report in Application No. 16202063.0, dated Jan. 31, 2019.

European Examination Report in Application No. 16202063.0, dated Jun. 11, 2019.

European Examination Report in European Patent Application No. 16202063.0, dated Nov. 11, 2019.

* cited by examiner

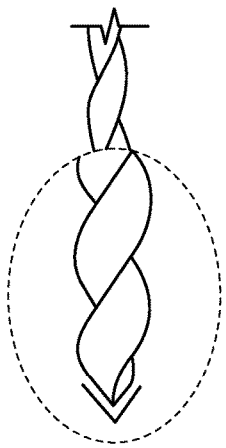 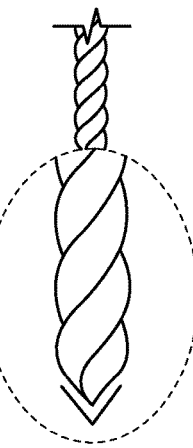 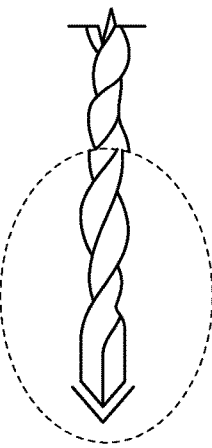 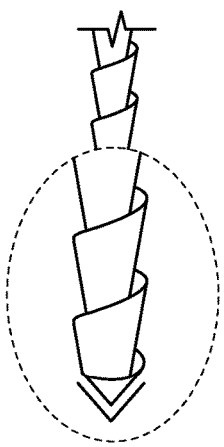
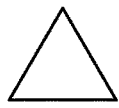 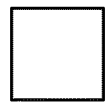 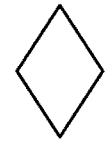 
FIG. 3A         FIG. 3B         FIG. 3C         FIG. 3D
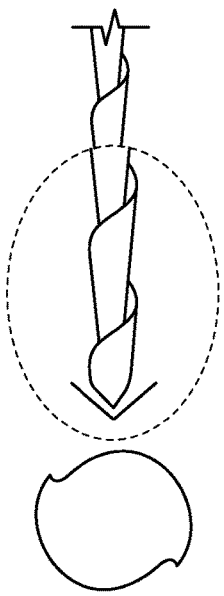 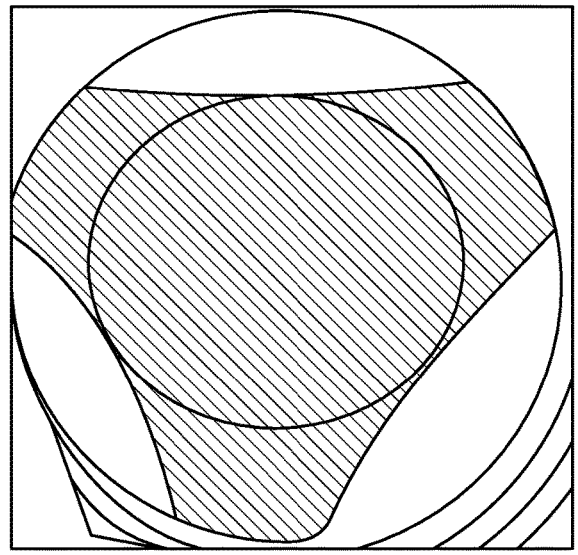
FIG. 3E         FIG. 3F
PRIOR ART

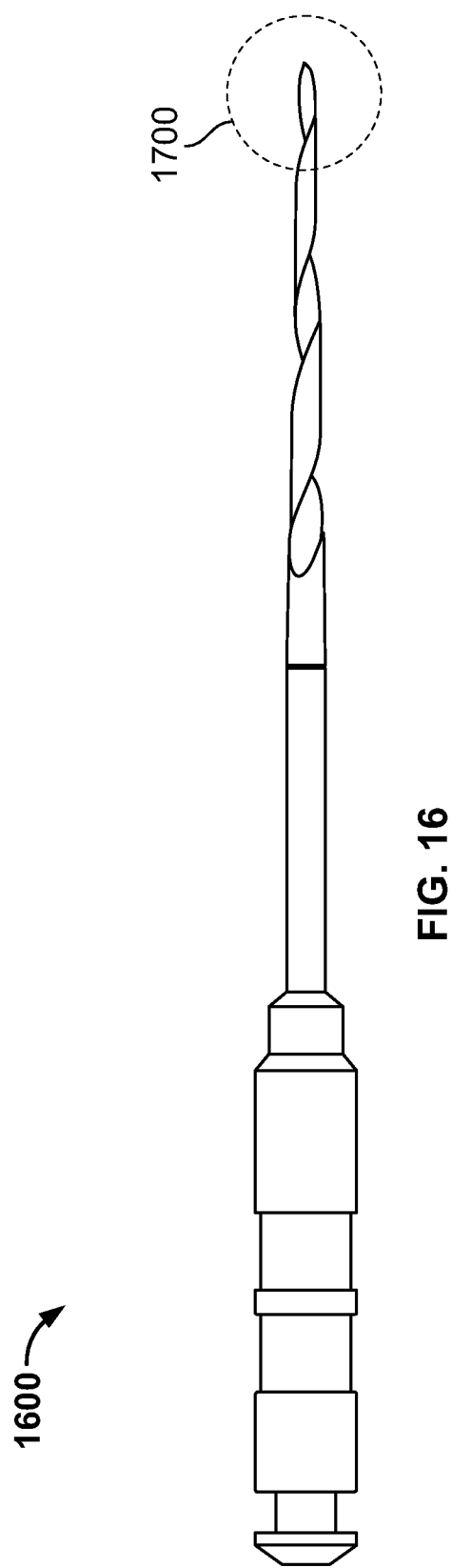

1700

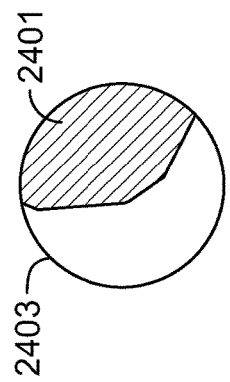
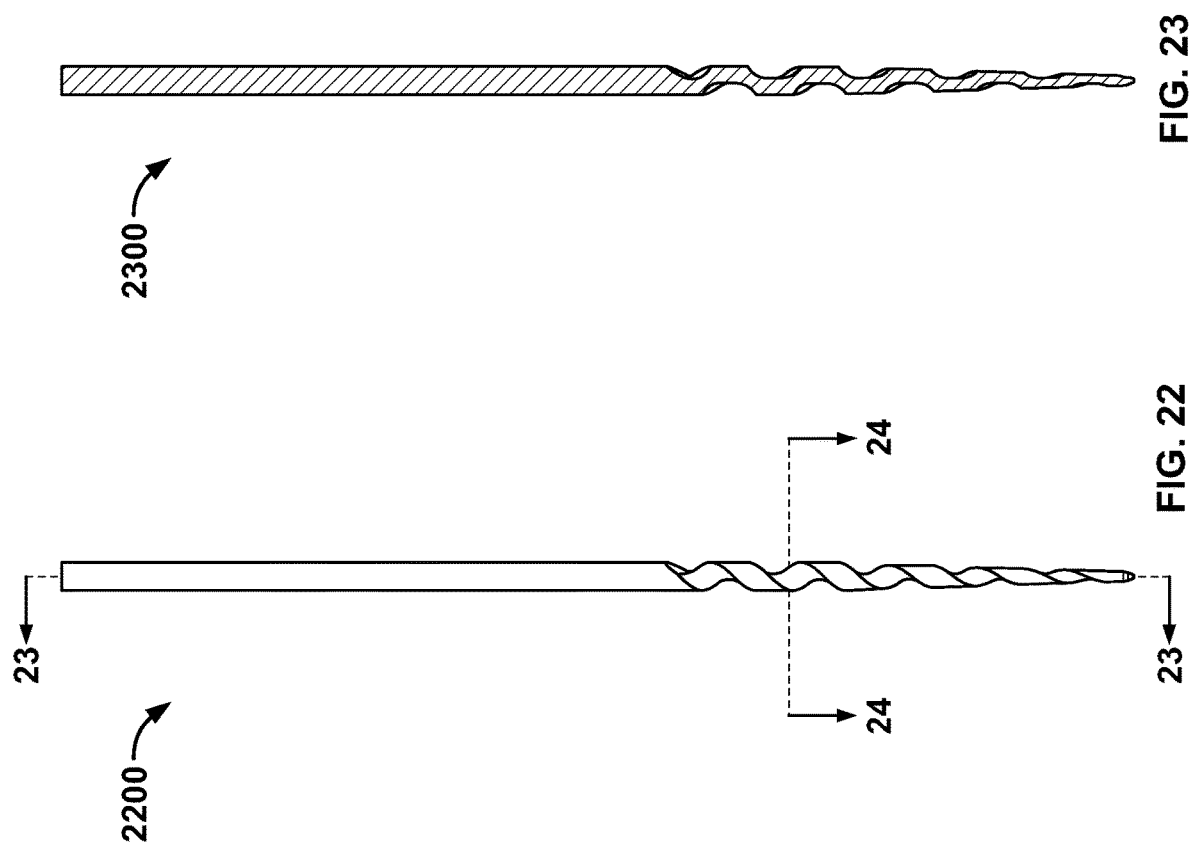

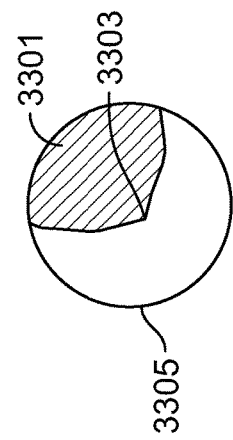
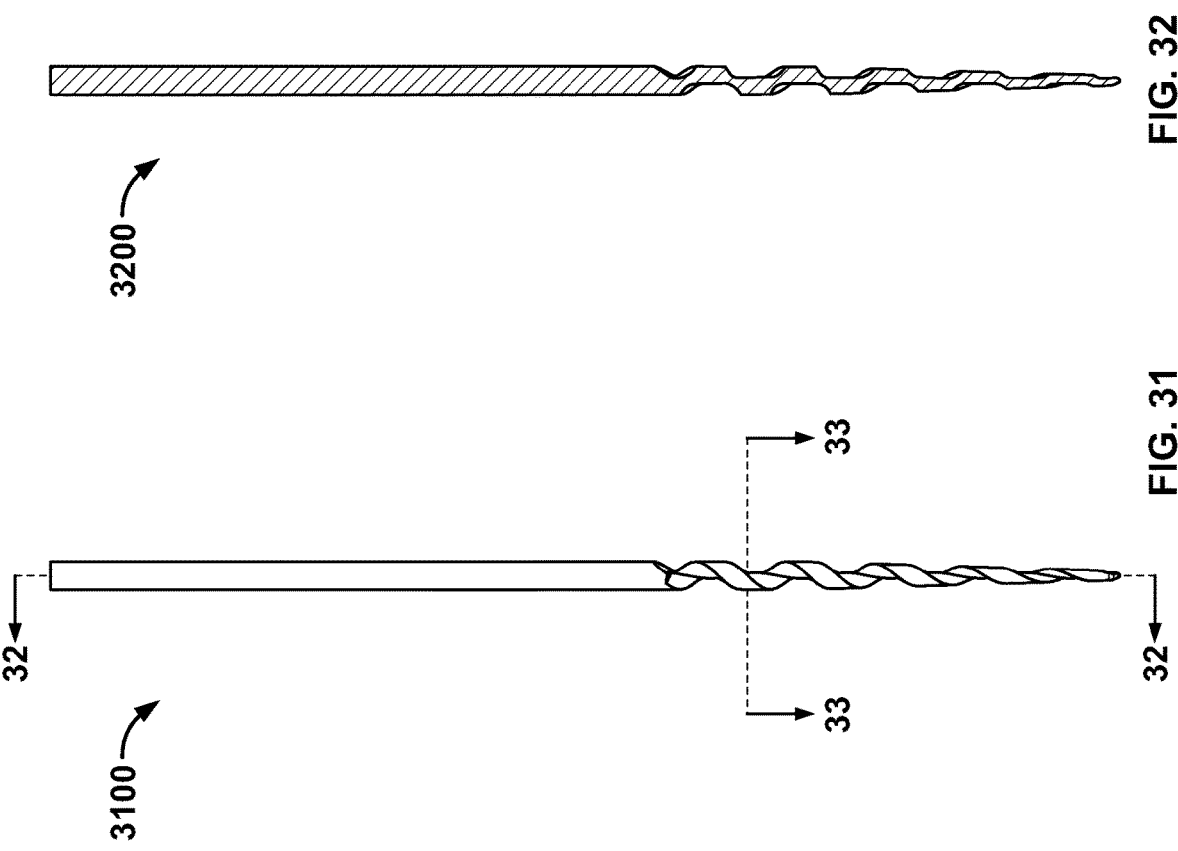
FIG. 33
FIG. 32
FIG. 31

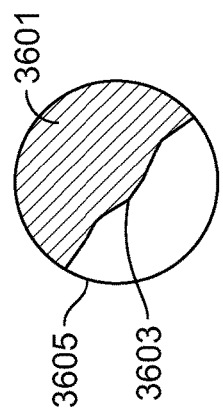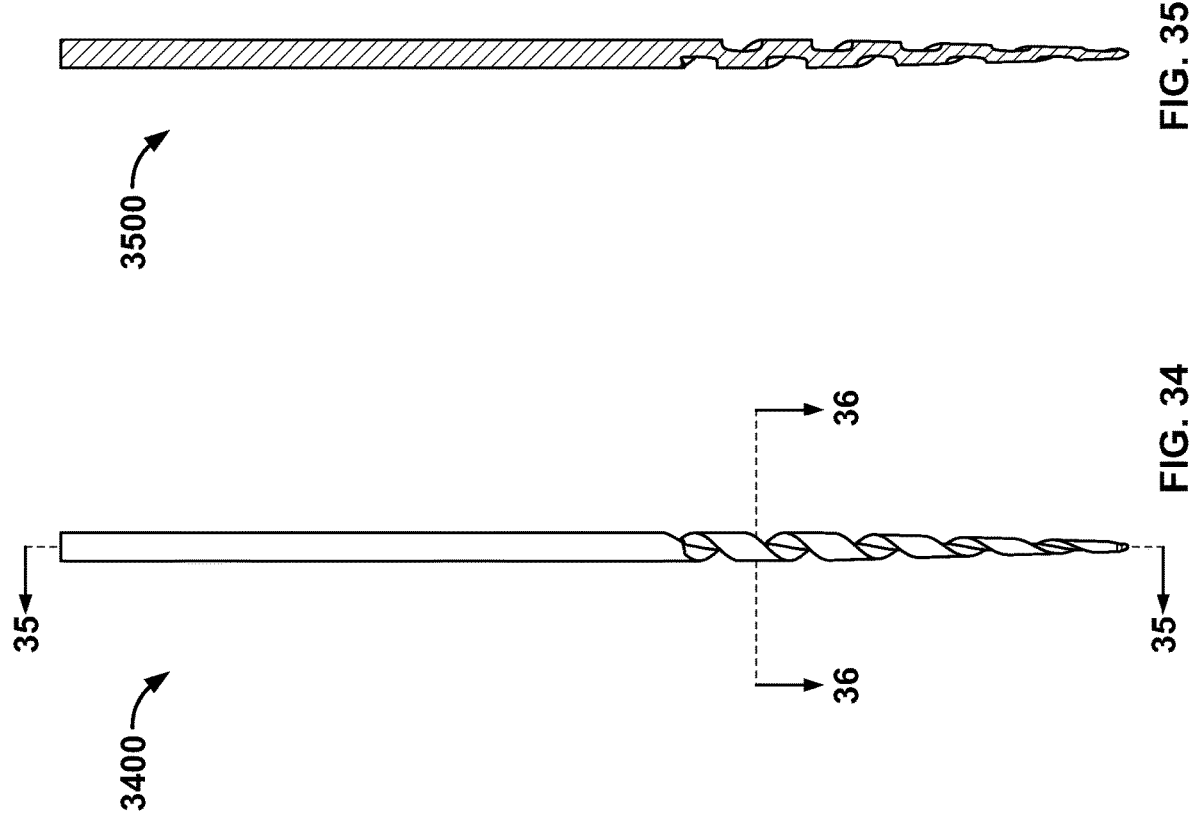

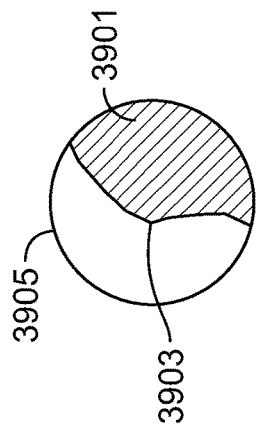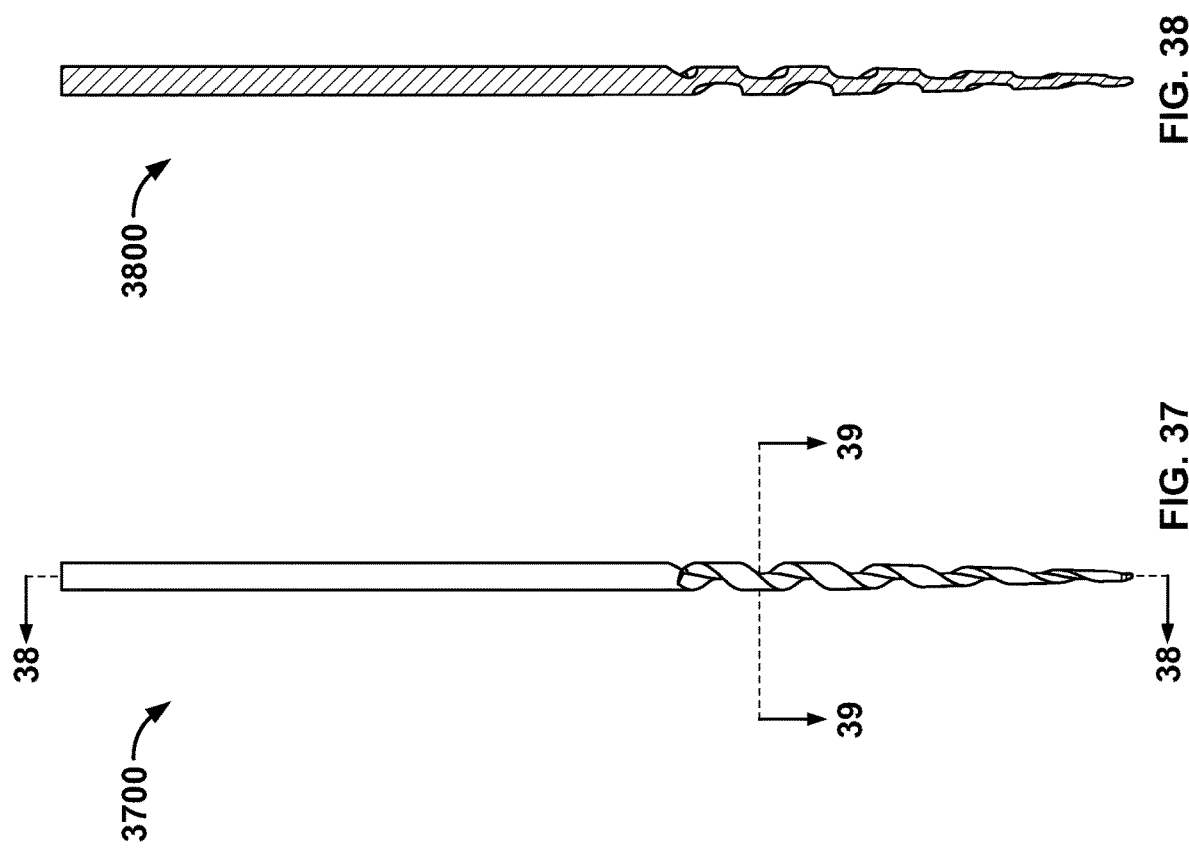

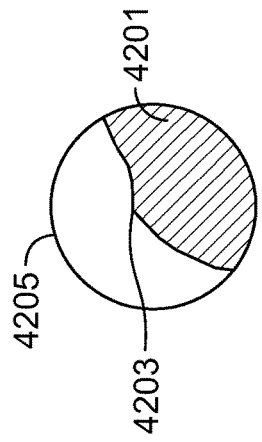
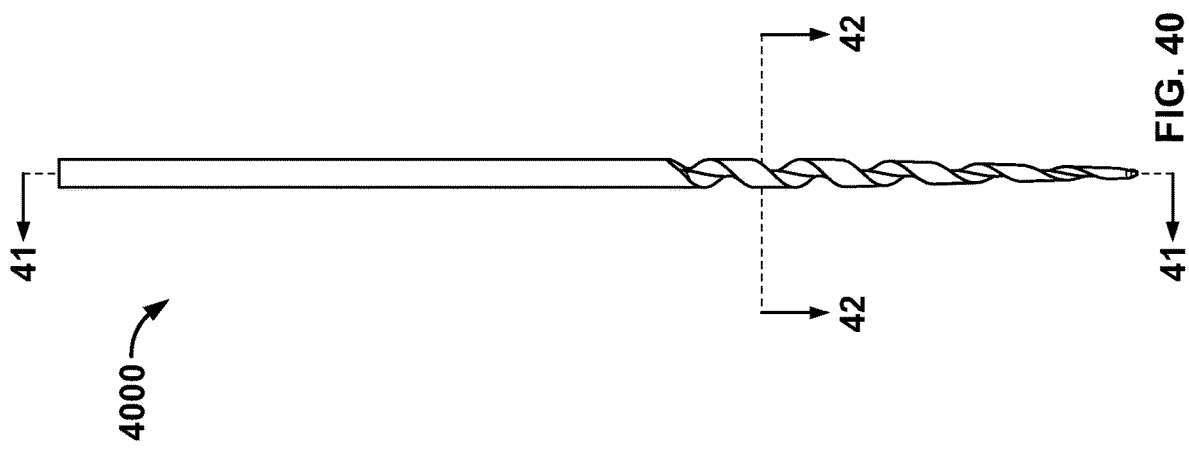
FIG. 42
FIG. 41
FIG. 40

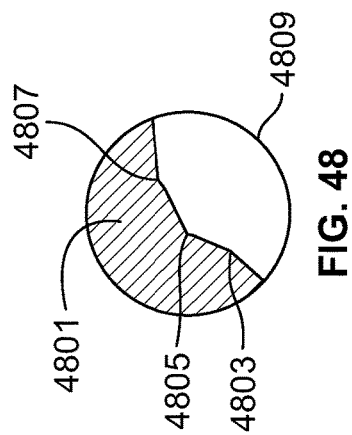
FIG. 48
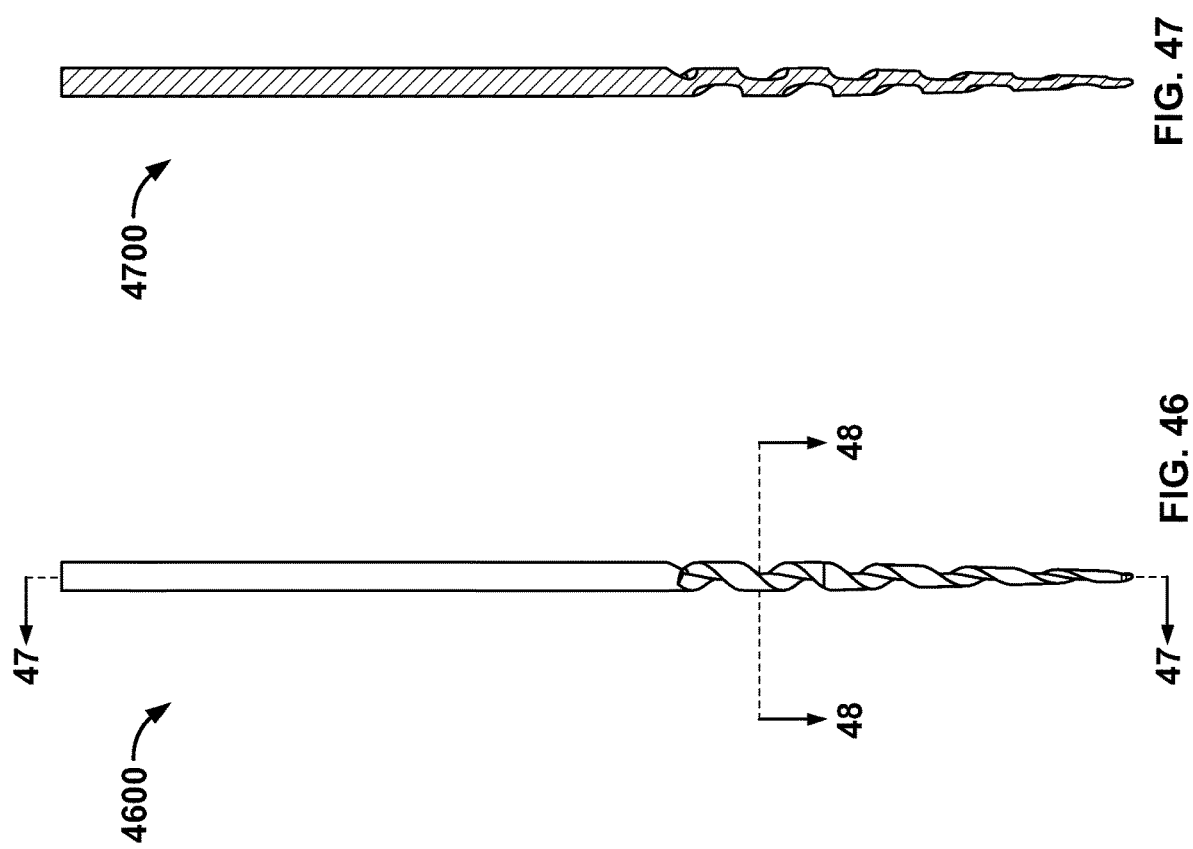
FIG. 47
FIG. 46

| Section | Position | A | B | C | D | E | F | G |
|---|---|---|---|---|---|---|---|---|
| 1 | 0.827 | 0.187 | 0.352 | 0.280 | 0.260 | 0.251 | 0.190 | 19.335 |
| 2 | 2.709 | 0.238 | 0.487 | 0.331 | 0.291 | 0.288 | 0.246 | 25.730 |
| 3 | 4.182 | 0.273 | 0.579 | 0.372 | 0.311 | 0.316 | 0.290 | 30.086 |
| 4 | 5.799 | 0.308 | 0.677 | 0.416 | 0.328 | 0.348 | 0.339 | 34.212 |
| 5 | 7.481 | 0.343 | 0.772 | 0.461 | 0.342 | 0.381 | 0.389 | 37.774 |
| 6 | 8.917 | 0.371 | 0.841 | 0.500 | 0.349 | 0.409 | 0.432 | 40.227 |
| 7 | 10.760 | 0.406 | 0.938 | 0.549 | 0.354 | 0.445 | 0.488 | 42.581 |
| 8 | 12.066 | 0.430 | 0.957 | 0.556 | 0.355 | 0.444 | 0.500 | 43.708 |
| 9 | 13.967 | 0.464 | 0.957 | 0.549 | 0.354 | 0.424 | 0.500 | 44.197 |
| 10 | 15.266 | 0.487 | 0.957 | 0.544 | 0.355 | 0.410 | 0.500 | 44.197 |

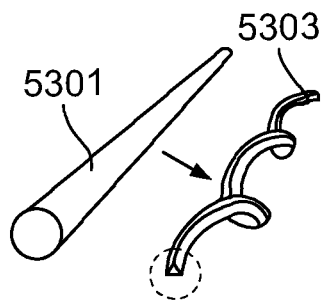
FIG. 53
 
FIG. 54  FIG. 55
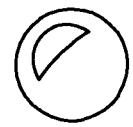 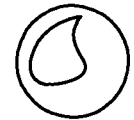
FIG. 56  FIG. 57
  
FIG. 58  FIG. 59  FIG. 60

FLUTED ENDODONTIC FILE

CROSS REFERENCE TO RELATED APPLICATIONS

This application is a nonprovisional of U.S. Provisional Application Nos. 62/262,899 filed on Dec. 3, 2015, and 62/277,473, filed on Jan. 11, 2016, both of which are hereby incorporated herein by reference in their entireties.

FIELD OF TECHNOLOGY

The present invention relates to the field of endodontic instrumentation, and more particularly to rotary files used to clean, remove debris from, and/or shape a tooth's root canal during a dental procedure.

BACKGROUND

A tooth may develop a carious lesion. The carious lesion may infect tooth tissue. A carious lesion may infect tooth tissue in a root canal of the tooth. If tooth tissue in the root canal is infected, the infected tissue should be removed from the tooth to stop further spreading of the carious lesion.

A dental procedure for removing infected tooth tissue from a root canal typically requires specialized tools. Such tools may include one or more endodontic files. Endodontic files are typically used to remove infected tooth tissue within root canal, tissue adjacent the root canal, and other parts of the tooth. Endodontic files are also used to drill into tooth tissue, shape the canal and clean the canal.

Endodontic files are typically rotated to remove infected tissue. The files may be rotated by hand and/or machine. A fluted end of an endodontic file may be used to shape the canal. The files typically have cutting edges for removing tissue in and/or near the root canal. The cutting edges are typically edges of helical flutes formed in the file.

Endodontic files used to remove infected tissue from the canal need to be small enough to remove infected tissue from the canal without damaging uninfected tooth tissue. An endodontic file should, preferably, when operating in the canal, preserve a natural curvature of the root canal and shape the canal with no or minimal foramen transportation. To preserve the natural curvature, endodontic files may be flexible to navigate the root canal curvature and/or tapered to "fit" into a root canal and reach the apical foramen of the canal without perforating the canal.

Due to their small size, endodontic files are susceptible to breaking in the canal. For example, in operation, when navigating curved sections of the canal, the file may be subject to combined torsion and bending stresses. Such stresses may break a file. Breakage of the file in the canal during the dental procedure may cause undesirable complications. For example, it may be difficult to extract a piece of the broken file from the canal.

Additionally, operation of an endodontic file within a root canal may generates debris that may cumulate (e.g., dislodged tissue) in the canal. The presence of the debris may increase torsion stresses on the file the probability of file breakage. As a result of the small size of the canal and presence of the file in the canal, it may be difficult to remove the debris while operating the file.

It would be desirable to provide an endodontic file that is flexible and less susceptible to breakage while operating in the canal. It would further be desirable to provide an endodontic file that channels debris out of the canal while operating in the canal.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIGS. 3A-3E show prior-art endodontic files;
FIGS. 3F-3J show prior-art endodontic file cross-sections;
FIG. 16 shows a side view of an illustrative file in accordance with principles of the invention;
FIG. 22 shows an illustrative file in accordance with principles of the invention;
FIG. 23 shows a cross-sectional view of FIG. 22 taken along lines 23-23;
FIG. 24 shows a cross-sectional view of FIG. 22 taken along lines 24-24;
FIG. 31 shows an illustrative file in accordance with principles of the invention;
FIG. 32 shows a cross-sectional view of FIG. 31 taken along lines 32-32;
FIG. 33 shows a cross-sectional view of FIG. 31 taken along lines 33-33;
FIG. 34 shows an illustrative file in accordance with principles of the invention;
FIG. 35 shows a cross-sectional view of FIG. 34 taken along lines 35-35;
FIG. 36 shows a cross-sectional view of FIG. 34 taken along lines 36-36;

FIG. 37 shows an illustrative file in accordance with principles of the invention;

FIG. 38 shows a cross-sectional view of FIG. 37 taken along lines 38-38;

FIG. 39 shows a cross-sectional view of FIG. 37 taken along lines 39-39;

FIG. 40 shows an illustrative file in accordance with principles of the invention;

FIG. 41 shows a cross-sectional view of FIG. 40 taken along lines 41-41;

FIG. 42 shows a cross-sectional view of FIG. 40 taken along lines 42-42;

FIG. 46 shows an illustrative file in accordance with principles of the invention;

FIG. 47 shows a cross-sectional view of FIG. 46 taken along lines 47-47;

FIG. 48 shows a cross-sectional view of FIG. 46 taken along lines 48-48;

FIG. 53 shows an illustrative blank that may be used to form a file in accordance with principles of the invention;

FIGS. 54-60 show illustrative cross-sections of a file in in accordance with the principles of the invention;

DETAILED DESCRIPTION OF THE DISCLOSURE

Figure 1B:
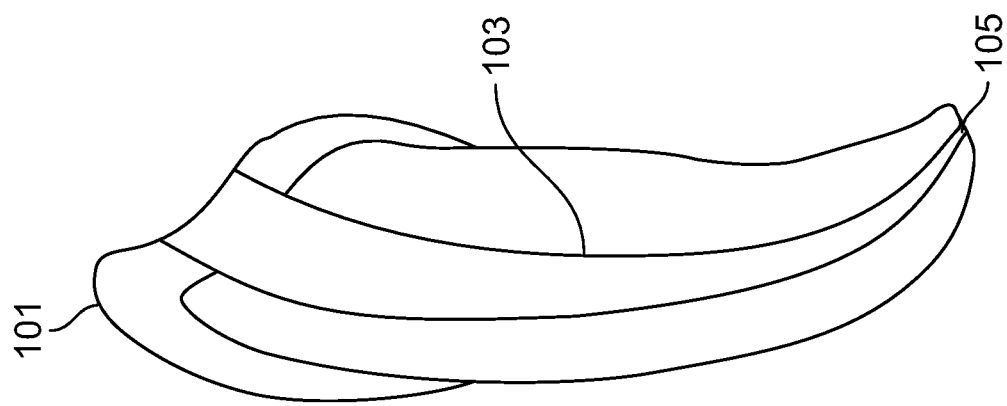
FIG. 1B shows a tooth after a root canal dental procedure.

The present disclosure relates to an endodontic file. In some embodiments, the file may be a single-flute endodontic file. In other embodiments, the file may have two or more flutes. The file may have enhanced debris-removing characteristics and/or enhanced flexibility characteristics.

The file may be fluted. A solid portion of the file that remains after the flute(s) of the file are formed is referred to herein as a "working length." The working length may extend between a terminal end of a shaft of the file and a tip of the file. A flute may define an indentation in the working length of the file. A flute may extend between two adjacent land surfaces in the file.

The file may include a single flute following a helical path of constant or variable pitch along the working length of the file. The file may include two or more flutes following a helical path of constant or variable pitch along the working length of the file. In other embodiments, the flute(s) of the file may include linear flutes (horizontal or vertical) or flutes that have any other suitable geometric shape.

In the embodiments where the file includes a single helical flute, the file may have a "coiled" appearance, and may be referred to alternately as a "coiled file." In some of these embodiments, the working length of the file may look as if it has been wrapped around a cone or mandrel. As a result, a longitudinal centerline of the file's working length may not lie along the file's central longitudinal axis (which, in some embodiments, is the file's axis of rotation), but instead may lie around or about it, leaving a central open space that the working length's helical cutting surfaces wrap around. Thus, the working length may be 'off-center' in relation to the central longitudinal axis.

In some embodiments, when the working length of the file is inserted into a root canal and rotated, the cutting surfaces formed by the flute may cut a shape into the root canal that is greater in diameter and taper than an actual diameter and taper of an elongate rod from which the file was formed.

The file may include a shank, a working length and a tip. The shank may define the central longitudinal axis. The working length may extend between the shank and the tip. In some embodiments, the working length may define a single flute, a land surface, and cutting edge(s). In some embodiments, the working length may include two or more flutes, two or more land surfaces, and two or more cutting edges.

In some embodiments, the file may include a groove extending through some or all of the working length. The groove may circumscribe at least a portion of a hollow space (hereinafter "fluted space") extending along the central longitudinal axis. The groove may extend longitudinally along some or all of the length of the working length.

For the purposes of the application, a land surface ("land") may be a surface extending along an outer face of the working length. The land may space a helical twist of a flute apart from an adjacent helical twist. In the embodiments where the file includes a single flute, the land of the file may be considerably larger than the land of an endodontic file having two or more flutes.

The file may define a plurality of geometric properties. Exemplary geometric properties include a central longitudinal axis, a groove, a fluted space, a plurality of cross-sections, a pitch, a taper, a helix angle, a removable area coefficient ("RAC"), and a number of helical twists of the flute along the file's working length. Any of the geometric properties detailed herein may be combined with any other geometric properties detailed herein to create a file with target performance parameters.

In some embodiments, one or more of the geometric properties of the file may be constant along the working length. In some embodiments, one or more of the geometric properties of the file may vary along the working length. For example, one or more of the size and/or shape of the file's cross-section, the pitch, the taper, the helix angle, the RAC and/or the location of a central axis of the grove may vary along the working length.

Geometric properties of the file, according to certain embodiments, described herein are properties that the file has at room temperature.

In some embodiments, a cutting edge of the file may have variable positive or negative rake angle along the working length. In some embodiments, the cutting edge of the file may have both positive and negative rake angles along the working length. The rake angle may an angle formed by an axis perpendicular to a surface of material to be removed (e.g., tooth tissue) and a cutting edge of the working length. The working length may have constant or variable RAC.

A cutting edge of the file, according to certain embodiments, may have a constant or variable helix angle along the working length. The helix angle may be an angle that the cutting edge forms with a long axis of the working length. The long axis may be an axis extending along an outer perimeter of the working length between the tip and the shank.

Along the working length, the file, according to some embodiments, may define one or more cross-sections. The cross section(s) may be symmetric cross-sections, asymmetric cross-sections, or symmetric and asymmetric cross-sections. The cross-sections may have any suitable geometric properties.

In some embodiments, a first portion of the working length may define cross-sections having a first number of sides. A second portion of the working length may define cross-sections having a second number of sides. The first number may be different from the second number. For example, a first portion of a working length of a transitional cross-section may have three-sided cross-sections. A second working length of the transitional cross-section file may have two-sided cross-sections.

The file, according to some embodiments, may include material properties such as one or both of shape memory and superelasticity. The file, according to some embodiments, may be machined from a tube, an elongated rod, a flat bar, a round bar, a square bar, a triangular bar, or any other suitable shaped blank. The machining of the file, according to some embodiments, may include one or both of heat treatment and variable heat treatment.

The file, according to certain embodiments, may be manufactured from a blank. The blank may be solid or hollow. The blank may be a tube, a cylinder, a flat sheet of material, or may have conical shape. The blank may have a circular cross-section, a square cross-section, a triangular cross-section, a rectangular cross-section, an oval cross-section, a diamond cross-section, a hexagon cross-section, or any other suitable cross-section. The cross-section of the blank may taper along the length of the blank.

The cross-section of the blank may be constant along the length of the blank. The cross-section of the blank may vary along the length of the blank. The cross-section may be any suitable shape, such as the cross-sections described above.

For example, in some embodiments, the blank may be manufactured having a varying cross-section. For example, a blank may be selected, or machined, such that at predetermined intervals along the length of the blank the cross-section of the blank is shifted in one direction (e.g., to the left), relative to a central axis of the blank. The cross-section of the blank may be shifted back in the opposite direction (e.g., to the right) at the next interval. The shifting may be offset by any suitable angle or any suitable distance. In some embodiments, the blank may be shifted by a fraction of a millimeter, by 1 mm, or by any suitable distance.

Using a blank with an off-center cross-section, when machining the file according to some embodiments, may support the machining of an off-center flute. Using a blank with an off-center cross-section may also support the machining of a file having a cutting edge defining a varying pitch. For a single-flute file, a cutting edge with varying pitch may assist the file to lodge less debris and be less susceptible to clogging when operating in the canal in comparison to a file with a centered cross-section.

Preferred construction materials for the blank, and the file, include stainless steel and any suitable nickel-titanium alloys such as nitinol, copper nitinol, nickel nitinol, or any other suitable nickel-titanium alloy. Such materials exhibit good flexibility, resilience and strength. Nickel-titanium alloys also exhibit superelasticity and shape memory (or controlled memory) and/or superelasticity. Flexibility and strength reduce the likelihood of file breakage when the file, according to some embodiments, is operating in the canal.

In some embodiments, the blank may be formed from heat treated Stainless Steel. The blank may be heat treated to exhibit specific superelastic or control memory properties when operating in a root canal. In some embodiments, the blank may be formed from heat treated Ni—Ti Shape Memory Alloy.

The file may be manufactured by grinding any of the blanks described above. The file may be manufactured using Electrical Discharge Machining (EDM) techniques on any of the blanks described above. For example, the file may be manufactured using one or more features of the EDM methods and apparatus that are shown and described in U.S. Pat. No. 7,207,111, which is hereby incorporated herein by reference in its entirety. The file may be manufactured using Electrochemical machining (ECM) techniques on any of the blanks described above. The file may be manufactured by laser cutting any of the blanks described above. The file may be manufactured using 3D printing.

The file may be manufactured by twisting any of the blanks described above. In some embodiments, the blank may be twisted around a mandrel or around its center to create the file. The blank may be a flat sheet of material, a hollow blank, or any of the blanks described above. For example, the file may be manufactured using one or more features of the heat treat methods and apparatus that are shown and described in U.S. Pat. No. 6,783,438, which is hereby incorporated herein by reference in its entirety. In some embodiments, the blank may be heat treated, twisted, and then heat treated again.

The file may include a single, helical flute. The file may include two or more flutes. A flute of the file may include a single pitch along the working length. Alternately, the file may include a variable pitch along the working length. The variable pitch may be manufactured in any suitable way. In exemplary embodiments, the variable pitch may be manufactured by varying the radial and/or longitudinal motion of a cutting tool used to form a flute in a blank described above. For example, movement of the cutting tool may vary relative to a central axis of the blank during any of the manufacturing processes described above.

In some embodiments where the file includes a single helical flute, an exemplary working length geometry may be narrow between the land surface and the flute to increase flexibility and decrease cyclic fatigue accumulation. The working portion may be more elongate around the central longitudinal axis to resist bending and unwinding from torsional stresses encountered during rotary cutting.

The file, according to certain embodiments, may include a land surface ("land"). The land may be a portion of a solid, tapered blank that was not removed when the flute was being formed during the manufacturing process. In some embodiments, such as where the file is a single flute file, the land may be longer relative to the flute along the long axis. In other embodiments, the flute may be longer relative to the land along the long axis.

The file, according to some embodiments, may include a fluted space, or 'anti-land'. The fluted space may wrap around the working length of the file along the central longitudinal axis. The fluted space may be visible in a cross-sectional view of the working length. In some embodiments, the fluted space may extend along a central longitudinal axis. In some embodiments, the fluted space may wrap around the central longitudinal axis and may not extend along the central longitudinal axis. In some embodiments, the fluted space may extend along, and wrap around, the central longitudinal axis. In some of the embodiments where the fluted space wraps around the central longitudinal axis, the fluted space may be off-center relative to the central longitudinal axis.

The file, according to certain embodiments, may include a cutting edge. A cutting edge may define a positive or negative rake angle. A cutting edge may define a positive rake angle when a file is rotated in a first direction (about a central longitudinal axis). The cutting edge may define a negative rake angle when the file is rotated in a second direction (about a central longitudinal axis) opposite the first direction.

The file, according to certain embodiments, may include two or more cutting edges. The cutting edge may be positioned on an edge of a flute included in the file, according some embodiments, and extend along the length of the flute. The cutting edge may be positioned on two edges of a flute included in the file and extend along the length of the flute.

In some embodiments, when a file is initially inserted into a tooth, only one of the cutting edges may engage and cut tooth tissue. However, as the file is rotated in the tooth, the file may begin to stretch and unwind. The stretching and unwinding of the file may bring other cutting edges (defined by edges or vertices in a cross section of the working length) of the file into contact with tissue, enabling them to begin engaging and cutting tissue as well.

According to certain embodiments, the geometric properties of the file may include a rake angle. The rake angle may be constant along the length of the file. The rake angle may vary along the length of the file. The rake angle may be negative or positive. The rake angle may have varying positive and/or negative values along the length of the file.

The geometric properties of the file, according to certain embodiments, may include a RAC. The RAC may be constant and/or variable along the working length. RAC may quantify a debris removal capability. The RAC may be defined as: RAC=Circumscribed Area/Material Cross-section Area/No. of Cutting Edges. More cutting edges of a file may translate into lower RAC value.

The cutting efficiency of the file, according to certain embodiments, may depend at least in part on the rake angle and the RAC value of the cutting edge. Obtaining a preferable cutting efficiency for a file may include balancing a rake angle and a RAC. A high cutting capability (positive rake angle and/or multiple cutting edges) is typically incompatible with a low RAC value. For example, a file with a high cutting capability may easily clog during shaping of a canal. The clogging may result from generating dentinal debris at a rate that is higher than the removal capability (e.g., a low RAC value). Clogging may lead to a jamming of the file, apical extrusion of the dentinal debris or even file breakage.

The geometric properties of the file may include the dimensions of the flute. For example, a depth of the flute may increase the RAC of the file. A depth of the flute may give a file an "off-center" geometric property. A depth of the flute may increase the flexibility of the file.

The file may include a tip. During shaping of a canal the tip may both enlarge the canal and guide the file through the canal. These tip functionalities may be accomplished by balancing various geometric features of the tip. Illustrative geometric features may include a rake angle of the flute's cutting edge, an angle and a radius of the tip's cutting edge and the proximity of the flute end to the tip end.

In some embodiments, the tip may be completely landed to form a complete circle by defining a conical shape with a small radius (also known as a 'complete tip'). The tip may thus have a rounded or circular shaped tip. A tip that forms a complete circle may be unable to cut material or may have poor cutting abilities.

In other embodiments, the tip may be shaped like a spoon ("spoon-shaped") (see for example FIGS. 7A and 7B). The spoon-shaped tip may include a half conical shape with a concave (relative to a longitudinal central axis of a file) radius. The spoon-shaped tip may be used to cut material during an endodontic procure. The spoon-shaped tip may have greater cutting capabilities in comparison to a complete tip.

The spoon-shaped tip may include a tip cutting edge. The tip cutting edge may extend along one or both sides of the tip and/or may be positioned at a distal end of the tip. The tip cutting edge may be shaped to reduce transportation and/or perforation of the canal during shaping. The tip cutting edge may, according to some embodiments, be designed to include a lower cutting efficiency than other parts of the file.

In some embodiments, wherein the file has a single flute, the spoon-shaped tip may be the resultant of the single flute design and associated cross-sections. The single flute may terminate prior to the tip, stop at the base of the tip, pass the base of the tip or extend through the tip.

The single flute design may allow for greater adjustability and control over tip design. A single flute design may allow a balance of patient safety (e.g., preservation of canal shape) and cutting considerations. A single flute design allows for a tip that includes less material (e.g., land area) than a typical file. Manufacturing a solid file blank, such as by grinding, twisting, EDM, 3D printing, or any other manufacturing process described herein, advantageously allows for a tip that includes more material (e.g., land area) than if the file was formed from a hollow tube.

The geometric properties of the file may include a pitch. For the purposes of the application, the term 'pitch' may refer to a distance between a point on the cutting edge and a corresponding point on an adjacent cutting edge. For a single-flute file, the point and the corresponding point may be separated by a 360 degree turn of the cutting edge.

In some embodiments, the pitch of the cutting edge may be constant. In other embodiments, the pitch of the cutting edge may vary along the working length of the file. For example, the pitch may increase progressively between the shank and the tip. Variable pitch may enhance debris removal.

In some embodiments, the file may define one or more pitch values. In exemplary embodiments, the pitch of the single flute file may range from 3 to 6 mm.

The pitch may define an angle ("pitch angle"). The pitch angle may be an angle between a central longitudinal axis and a long axis of the working length (extending longitudinally along an outer surface of the working length). The pitch angle may be constant or may vary along the working length. In exemplary embodiments, the pitch angle may begin close to the shank at a 30-degree angle (relative to a central longitudinal axis of the file) and then become 50-degrees at the tip.

In some embodiments, the geometric properties of the file may include a plurality of cross-sections along the working length. A cross-section of the working length may show the shape of the solid material remaining after flute(s) were formed along the working length. The cross-sections may be perpendicular to the central longitudinal axis and along the working length of the file. A cross-section may be symmetric or asymmetric and have two or more sides.

In exemplary embodiments, a cross-section may have an area of 20% to 75% of the total area circumscribed by a circular perimeter of the cross-section. In some embodiments, more surface area of the cross-section will result in a stronger file. In some embodiments, more surface area behind a cutting edge of the file will result in a stronger file.

In certain embodiments, the shape of a cross-section of the working length may vary along the file's central axis. The shape may vary continuously along the working length.

In some embodiments, the working length may include a first portion defining cross-sections having a first number of sides and a second portion defining cross-sections having a second number of sides. The first number may be different from the second number.

For example, in exemplary embodiments, a tip of a file may have a rectangular cross-section and a portion of the file closest to the shank may have a triangular cross-section. These cross-sections may produce lower torsional stress at these points relative to other cross-sectional shapes. In some embodiments, varying cross-sections may be formed by grinding a solid blank or by any of the other machining methods described herein.

Each cross-section taken of the working length may be one-sided, two-sided, three-sided, four-sided, five-sided, or have any suitable number of sides (when observing a planar view of a cross-section). Each side of the cross-section may be straight or convex/concave (relative to a center of the cross-section, or any point within an area of the cross-section). The cross-section may be off-center. An off-center cross-section may increase flexibility of the file.

The cross-sections of most prior-art endodontic files are symmetric or non-symmetric and centered about a longitudinal center axis of a file (see, for example, FIGS. 3F-3J). Off-center center cross sections disclosed herein may be symmetric or asymmetric shapes that are not centered about a longitudinal center axis of a file. An off-center cross-section may or may not intersect the central longitudinal axis.

In exemplary embodiments, a working length of the file may have circular cross-sections, square cross-sections, triangular cross-sections, rectangular cross-sections, oval cross-sections, diamond cross-sections, hexagon cross-sections, or any other suitable cross-section. The cross-sections may be off-center. The area of the cross-sections may decrease along the length of the blank.

The cross-section may be off-center in relation to the central longitudinal axis. In some embodiments, the off-center cross-section may be manufactured by twisting or grinding a coiled blank, or by any other manufacturing method disclosed herein.

Off-center cross-sections may give a file enhanced debris removal capabilities. For example, off-center cross-sections may assist the fluted portion of a file in capturing or channeling out cut tissue during an endodontic procedure. This may be the result of a file's training edge having a greater area available for loading debris. Enhanced capabilities of capturing or channeling cut tissue may assist a practitioner in advancing a file further along a canal in a tooth (in comparison to a prior-art file) prior to necessitating a file's removal and cleaning.

In some embodiments, when the working length is viewed in cross-section, one of the sides of the cross-section may correspond to the land. The side of the cross-section corresponding to the land may have convex shape. In some embodiments, the side of the cross-section corresponding to the land may circumscribe a portion of a reference circle perimeter.

The working length may include symmetric cross-sections (see, for example, FIGS. 5-9) along its length. The working length may include symmetric, off-center cross-sections (see, for example, FIGS. 5-7) along its length. A symmetric cross-section of a working length may be positioned at a constant or a variable distance from the central longitudinal axis to a middle point or the inner vertex of the cross-section (see, for example, FIGS. 5-9).

The working length may include asymmetric cross-sections (see, for example, FIGS. 10-13) along its length. The working length may include asymmetric, off-center cross-sections along its length. The asymmetric cross-section of a working length may be positioned at a constant or variable distance from the central longitudinal axis to a middle point or the inner vertex of the cross-section.

A cross-section may include a circular side. A cross-section may include a concave side (relative to a point within the cross-section). A cross-section may include two or more concave sides. A cross-section may include a convex side (relative to a point within the cross-section). A cross-section may include two or more convex sides.

A cross-section may include a circular side and two convex sides. A three-sided cross-section may include one circular side, one convex side and one concave side. A three-sided cross-section may change to a two-sided convex or concave cross-section toward the tip end of the file.

A three-sided cross-section may include three vertices. A first vertex may be a cutting edge. A second vertex may be a positioned at or near a land portion of the cross-section. In some embodiments, the second vertex may also be a cutting edge. A third vertex may be an inner vertex.

In some embodiments, the file may include cross-sections with a concave side along a first portion of the working length and cross-sections with a convex side along a second portion of the working length. The convex side may change to being a concave side along the working length. In exemplary embodiments, the convex side may change to a concave side closer to the tip of the file.

In some embodiments, the working length of the file may include a first length and a second length. The first length may have two flutes and the second length may have one flute. The first length may comprise approximately two-thirds of the working length, and the second length may comprise approximately one-third of the working length. The first length may comprise approximately one-third of the working length, and the second length may comprise approximately two-thirds of the working length. The first length and the second length may each comprise approximately half of the working length. The first length may add strength to a file. The second length may give a file enhanced flexibility and debris removal characteristics. One end of the first length may be adjacent the shank, and one end of the second length may be adjacent the tip. Alternatively, one end of the first length may be adjacent the tip and one end of the second length may be adjacent the shank.

In some embodiments, the longitudinal dimensions of the single-fluted and double-fluted portions of the file may depend at least in part on the taper of the file. A file with a shallow taper may have a large single-fluted length and a small double-fluted length. A file with a steep taper may have a small single-fluted length and a large double-fluted length.

In some embodiments, the working length of the file may include a first, second and third length. The second length may be positioned in between the first and third lengths. The first and third length may have two flutes and the second length may have a single flute. Alternatively, the first and third length may have a single flute and the second length may have two flutes.

In exemplary embodiments, a file including a three-sided cross-section may be constructed from heat treated Stainless Steel and/or Ni—Ti Shape Memory Alloy. The file may include a symmetric or asymmetric off-center three-sided cross-section. An off-center three-sided cross-section may have an area of 20% to 75% of the total area circumscribed by a circular perimeter of the cross-section.

In exemplary embodiments, a file may define an off-center, three-sided cross-section (see, for example, FIGS. 8-13). The three-sided cross-section may be symmetrical or asymmetrical. The cross-section may have an area of 20% to 75% of the total area circumscribed by a circular perimeter of the cross-section.

In exemplary embodiments, a file may include an endodontic file having a standard (per ISO 3630-1) or non-standard size and taper. A file may include one flute of constant or variable pitch. A file may include an off-center cross-section. The off-center cross-section may have an area that is 20% to 75% of a total area of a circular perimeter that encloses the cross-section.

In some embodiments, cross-sections of the working length may not include any vertices.

In some embodiments, cross-sections of the working length may include one or more vertices. A vertex may be an angular point defined by the cross-section and positioned at the junction of two sides of the cross-section. The cross-sections of the file may define one, two, three, four, five, or any other suitable number of vertices. In some embodiments, a first portion of the working length may define cross-sections having a first number of vertices. In some of these embodiments, a second portion of the working length may define cross-sections having a second number of vertices. At least one of the vertices may be a cutting edge.

In some embodiments, the geometric properties of the working length of the file may include one or more inner vertices and one or more outer vertices. An inner vertex may be a vertex that does not lie on a reference circular perimeter. An outer vertex may be a vertex that lies on the reference circular perimeter. The reference circular perimeter may be a circle that circumscribes the cross-section and includes some or all of a side of the cross-section corresponding to the land surface of the working length.

In some embodiments, an inner vertex may be positioned at or near a central longitudinal axis. In some embodiments, an inner vertex may be positioned at a distance from the central longitudinal axis. In some embodiments, a distance between the inner vertex and the central longitudinal axis may be constant along the working length. In other embodiments, a distance between the inner vertex and the central longitudinal axis may vary along the working length. The distance may vary within the range of the initial value +/−65% from the centerline.

In exemplary embodiments, an asymmetric off-center three-sided cross-section may include an inner vertex. The inner vertex may be positioned at a constant distance from the central longitudinal axis. The inner vertex may be positioned at a distance from the central longitudinal axis that varies along the working length of the file. The distance may vary within the range of the initial value+/−65%. The asymmetric off-center three-sided cross-section may be constructed from heat treated Stainless Steel and/or Ni—Ti Shape Memory Alloy.

Figure 6:
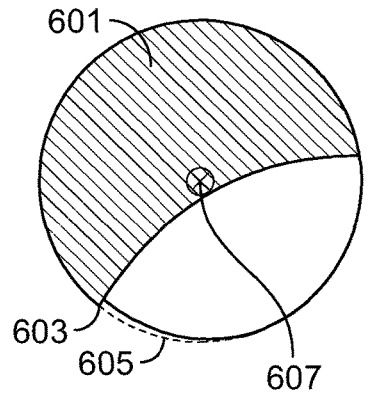

In exemplary embodiments, the file may include a symmetrical, off-center cross-section (see, for example, FIG. 6). The distance from a central longitudinal axis to the midpoint of the cross-section may be constant along the file. The distance may vary within the range of +/−65% of the initial value from a central longitudinal axis.

The geometric properties of a file may include a taper. The file may taper—i.e. reduce in thickness—along the working length. The taper may be constant or may vary along the working length. Variable taper may be defined based on a variable distance from an inner vertex of the cross-section of a file to the central longitudinal axis.

In some embodiments, the file taper may be described by two or more tapers. Each taper may be associated with a face of a file. For example, a first taper may be a taper of an outer face of a file, such as the land surface ("outer taper"). Additional tapers may be tapers of the one or more inner faces of the working surface ("core tapers"). In exemplary embodiments, a file with a three-sided cross-section may define three tapers—one outer taper and two core tapers.

In some embodiments, one or both of the outer taper and the core taper(s) may be constant along the working length of a file. One or both of the outer taper and the core taper(s) may vary along the working length of a file. For example, the outer taper and/or the core taper(s) may increase progressively between the shank and the tip.

In some embodiments, the outer taper may be the same as one or more of the core tapers. In other embodiments, the core taper may be different from the SF taper. For example, the taper of the inner face(s) of a file may vary differently or independently from the taper of the outer face of a file.

The file may have any suitable number of core tapers. In exemplary embodiments, the file may include two, three or six different core tapers. Different core tapers may allow for adjustment in file flexibility in targeted areas of the file and less flexibility in another area of the file.

The file may include a groove extending along some or all of the working length. In some embodiments, a cross-section of the working length may include a concave side (relative to a center of the cross-section, or any point within an area enclosed by the cross-section) positioned between two inner vertices (see, for example, FIG. 7). The concave side positioned between the two inner vertices may define the groove.

The groove may be symmetrical. The groove may be asymmetrical. The grove may have a constant or variable taper. The groove may circumscribe a portion of the fluted space of the file.

The grove may extend along some or all of the working length. A center or approximate center of a groove may be positioned at a constant distance from the central longitudinal axis. A center or an approximate center of a groove may be positioned at a variable distance from the central longitudinal axis. In some embodiments, the groove may intersect the central longitudinal axis. In some embodiments, the groove may not intersect the central longitudinal axis.

The position of the groove may be measured from a vertex of the working length. The groove may be positioned to a right or left side of a mid-point of a cross-section.

The groove may facilitate removal of dentinal debris and necrotic tissue during a canal shaping process. For example, debris may flow from an apical foramen of the tooth through the groove. Debris flowing through the groove may exit the groove at or near a coronal area of the tooth. The groove may also be utilized to channel gutta-percha or other sealants into the canal during obturating and sealing of the canal. The groove may also be used to shovel dentinal debris and necrotic tissue and, in some embodiments, retain the shoveled material within the working length.

In exemplary embodiments, a distance from a central longitudinal axis to a center of a groove in a cross-section may be constant along a length of the file. In other embodiments, the distance from the central longitudinal axis to the center of the groove may vary within a range of +/−65% of the initial value from the longitudinal axis.

In some embodiments, the file may include a hollow core extending through some or all of the file's working length.

In some embodiments, the apparatus may include a file defining a central longitudinal axis and including a working length extending along the central longitudinal axis. The working length may include a single flute extending along the central longitudinal axis. The working length may define an off-center cross-section along the central longitudinal axis. The cross-section may include three vertices.

One of the three vertices may be an inner vertex positioned apart from the central longitudinal axis. One of the three vertices may be an inner vertex and may be aligned with the central longitudinal axis.

The cross-section may define an area. The area may include the central longitudinal axis. The area may not include the central longitudinal axis.

The working length may define a plurality of off-center cross-sections along the central longitudinal axis. The plurality of off-center cross-sections may include the cross-section. In some embodiments, distances between an inner vertex of each the plurality of off-center cross-sections and the central longitudinal axis may be constant along the working length. In some embodiments, distances between an inner vertex of each the plurality of off-center cross-sections and the central longitudinal axis vary along the working length.

In certain embodiments, the file may comprise a spoon-shaped tip. The spoon-shaped tip may be positioned at an end of the working length and be configured to cut tooth tissue. In some embodiments, the spoon-shaped tip may have a half conical shape with a concave radius and include a tip cutting edge extending along a side of the tip.

The cross-section may define a first side, a second side and at third side. The first side and the second side may both be convex relative to a point within the cross-section. The first side may be concave relative to a point within the cross-section. The first side and the second side may both be concave relative to a point within the cross-section. One or more of the first side, the second side and the third side may be either convex or concave (relative to a point within the cross-section) or straight. In some embodiments, one or more of the first side, the second side and the third side may be wavy, curvy, or define any other suitable shape.

The file may include a fourth vertex. In some of these embodiments, one of the three vertices may be a first inner vertex. The fourth vertex may be a second inner vertex. A side of the cross-section extending between the first inner vertex and the second inner vertex may be concave relative to a point within the cross-section. In some of these embodiments, the cross-section may define an area that does not include the central longitudinal axis. In some of these embodiments, the cross-section may define an area that includes the central longitudinal axis.

The cross-section may comprise an area of 20 to 75% of a total area circumscribed by a circle surrounding the cross-section.

In some embodiments, the working length may include a first portion extending along the central longitudinal axis and a second portion adjacent the first portion and extending along the central longitudinal axis. The working length may define a first plurality of cross-sections along the first portion, the first plurality of cross-sections including the cross-section and having three vertices. The working length may define a second plurality of cross-sections along the second portion, the second plurality of cross-sections having two vertices.

In some embodiments, a shape of the cross-section may be selected from the group consisting of a triangle, square and diamond.

In some embodiments, the apparatus may include a file defining a central longitudinal axis and including a working length extending along the central longitudinal axis. The working length may include a first portion extending along the central longitudinal axis and a second portion adjacent the first portion and extending along the central longitudinal axis. The working length may define a first plurality of cross-sections having a first number of sides along the first portion. The working length may define second plurality of cross-sections having a second number of sides along the second portion.

The working length may include a single flute extending along the central longitudinal axis. The single flute may wrap around the central longitudinal axis and define a cutting edge. The first plurality of cross-sections may have three sides. The second plurality of cross-sections may have four sides.

In some embodiments, each of the first plurality of cross-sections may define at least one convex side relative to a point within the corresponding cross-section. In some embodiments, each of the second plurality of cross-sections may define at least one concave size relative to a point within the corresponding cross-section.

The working length may include a single flute extending along the first portion. The working length may include two flutes extending along the second portion. The first portion may extend away from a shank of the file. The second portion may include a tip of the file. The working length may include a double flute extending along the first portion. The working length may include a single flute extending along the second portion. The first portion may extend away from a shank of the file. The second portion may include a tip of the file.

In some embodiments, a first portion of the working length may comprise two-thirds of the length and the second portion comprises one-third of the working length. In some embodiments, a first portion of the working length may comprise one-thirds of the length and the second portion comprises two-thirds of the working length.

In some embodiments, the working length may include a single flute. The flute may pass through a tip region of the file.

Apparatus and methods described herein are illustrative. Apparatus and methods in accordance with the invention will now be described in connection with the FIGS. The FIGS. show illustrative features of apparatus and method steps in accordance with the principles of the invention.

The steps of the methods may be performed in an order other than the order shown and/or described herein. Some embodiments may omit steps shown and/or described in connection with the illustrative methods. Some embodiments may include steps that are neither shown nor described in connection with the illustrative methods. Illustrative method steps may be combined. For example, one illustrative method may include steps shown in connection with another illustrative method.

Some apparatus may omit features shown and/or described in connection with illustrative apparatus. Some embodiments may include features that are neither shown nor described in connection with the illustrative methods. Features of illustrative apparatus may be combined. For example, one illustrative embodiment may include features shown in connection with another illustrative embodiment.

Apparatus may involve some or all of the features of the illustrative apparatus and/or some or all of the steps of the illustrative methods. Methods may involve some or all of the features of the illustrative methods and/or some or all of the steps of the illustrative apparatus.

Apparatus and methods will now be described with reference to the accompanying figures, which form a part hereof. It is to be understood that other embodiments may be utilized and that structural, functional and procedural modifications may be made without departing from the scope and spirit of the present disclosure.

Figure 1A:
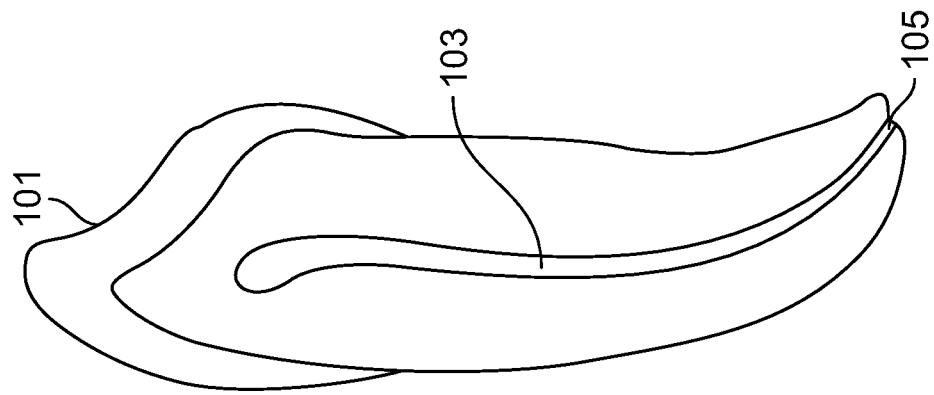
FIG. 1A shows a tooth prior to a root canal dental procedure.

FIG. 1A shows a tooth. The tooth includes coronal area 101, root canal 103 and apical foramen 105. The root canal 103 is a typical root canal before a root canal dental procedure is performed.

FIG. 1B shows a tooth after a root canal dental procedure is performed. The root canal dental procedure may include opening coronal area 101 of the tooth to access root canal 103. The dental procedure may include negotiating the infected root canal 103 with an endodontic file. The endodontic file may be operated by hand or machine. At this point in the dental procedure, it may be advantageous to negotiate the file as close as possible to apical foramen 105.

The dental procedure may include using the file to progressively shape and remove infected/necrotic pulp in root canal 103. It may be preferable to perform the dental procedure while keeping apical foramen 105 as small as possible. The dental procedure may include obturating and sealing of root canal 103.

Figure 2:
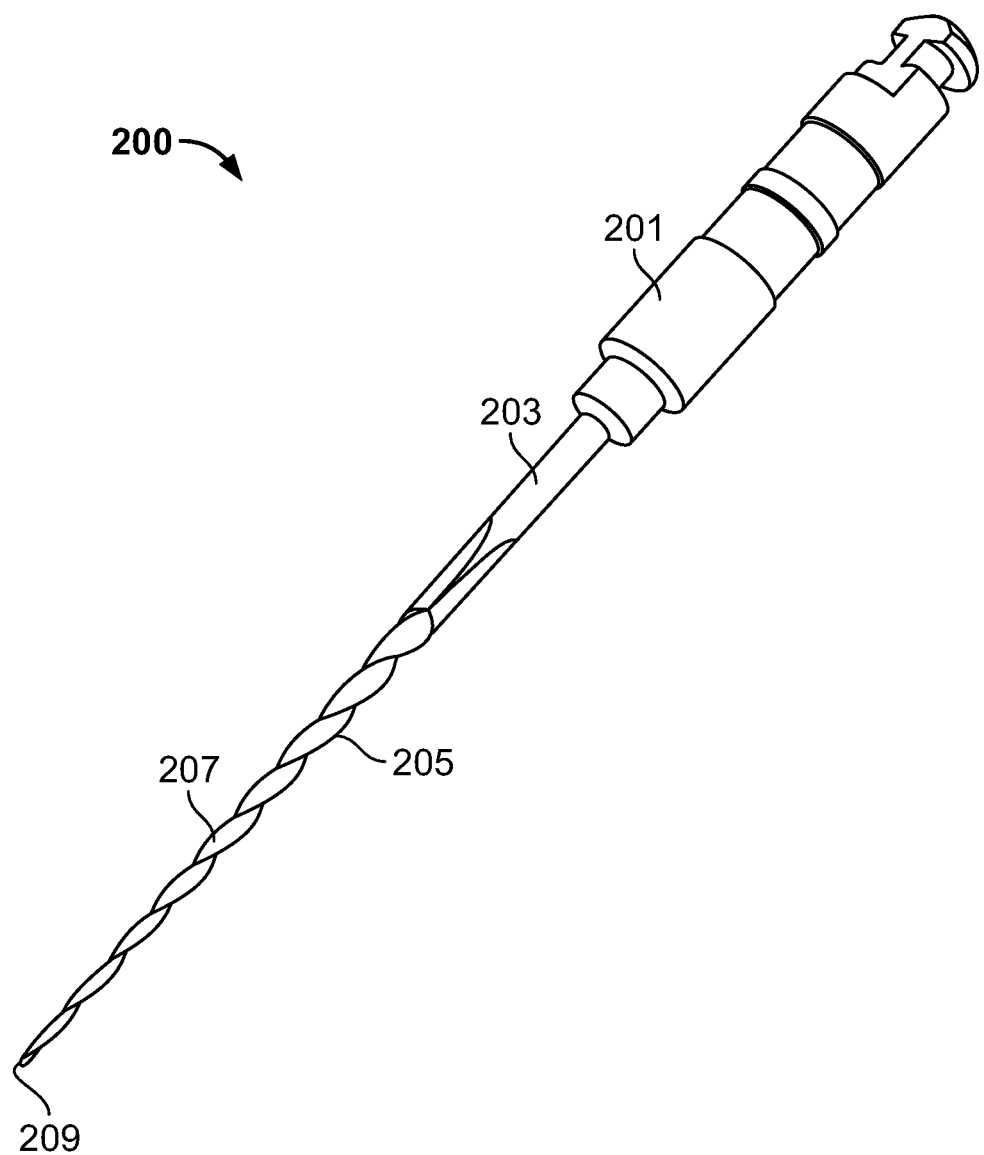
FIG. 2 shows a prior-art endodontic file.
Figure 3G:
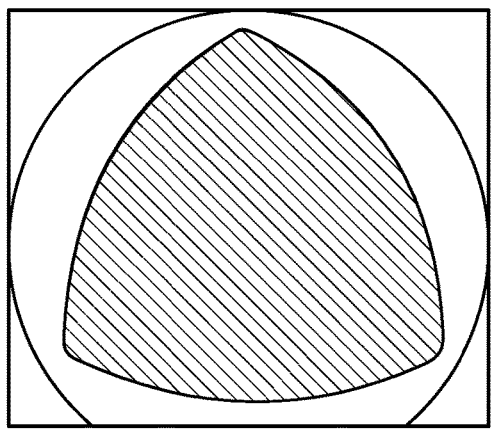
Figure 3H:
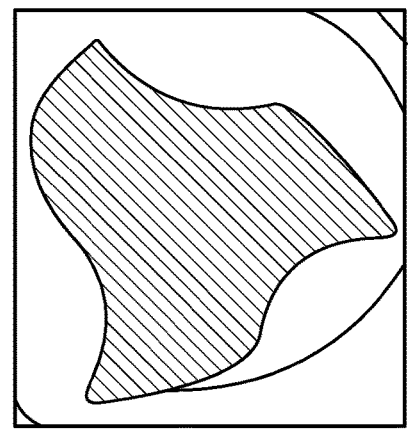
Figure 3I:
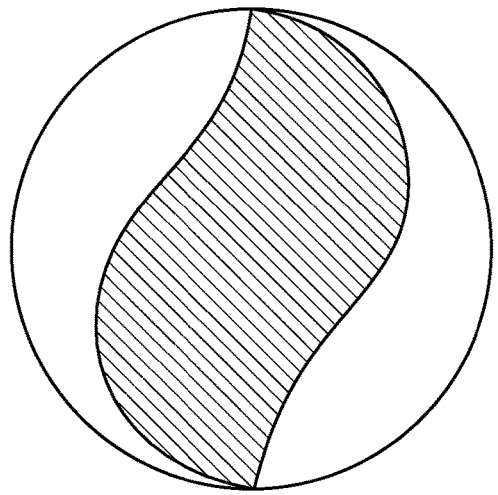
Figure 3J:
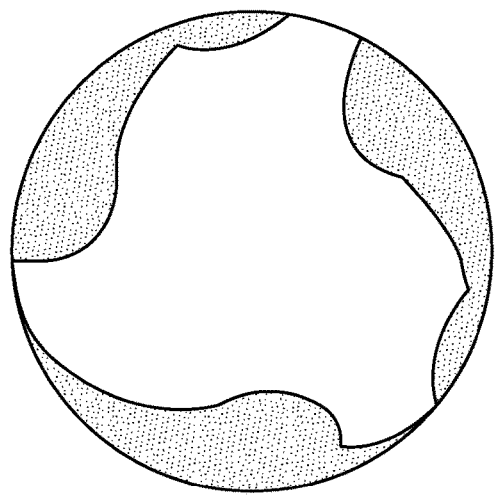

FIG. 2 shows geometric features of generic endodontic file 200 that may be utilized to shape a root canal. File 200 includes hand piece engagement 201. Hand piece engagement 201 may be used to connect file 200 to machinery that rotates file 200. The machinery may rotate file 200 at various speeds and/or in various directions.

File 200 includes shank 203. File 200 also includes a working length extending between shank 203 and tip 209. The working length may include may include two or more flutes 207. A flute 207 may include one or more cutting edges 205. Tip 209 may be a portion of file 200 operating closest to the apical foramen 105 (shown in FIGS. 1A and 1B) when file 200 is operating in root canal 103 (shown in FIGS. 1A and 1B).

FIGS. 3A-3E show prior-art endodontic file designs and associated cross-sectional views. FIGS. 3F-3J show prior-art endodontic file cross-sectional views. Cross-sectional views may be described with respect to an area of the cross-section relative to a reference circular perimeter that encircles the cross-sectional view or profile.

Existing endodontic files typically include two or more cutting edges. Multiple cutting edges reduce the file's RAC value. Existing endodontic files typically include two or more flutes. Generally, each flute has two edges. One cutting edge and one trailing edge, respectively. A triangular cross-section file, as shown in FIG. 3A, has three flutes and 6 theoretical edges. However, due to the triangular shape of the cross-section, the trailing edge of flute 1 is also the cutting edge of the flute 2, the trailing edge of the flute 2 is also the cutting edge of the flute 3, and the trailing edge of flute 3 is also the cutting edge of flute 1. Therefore, a triangular file typically includes three cutting edges.

Figure 4:
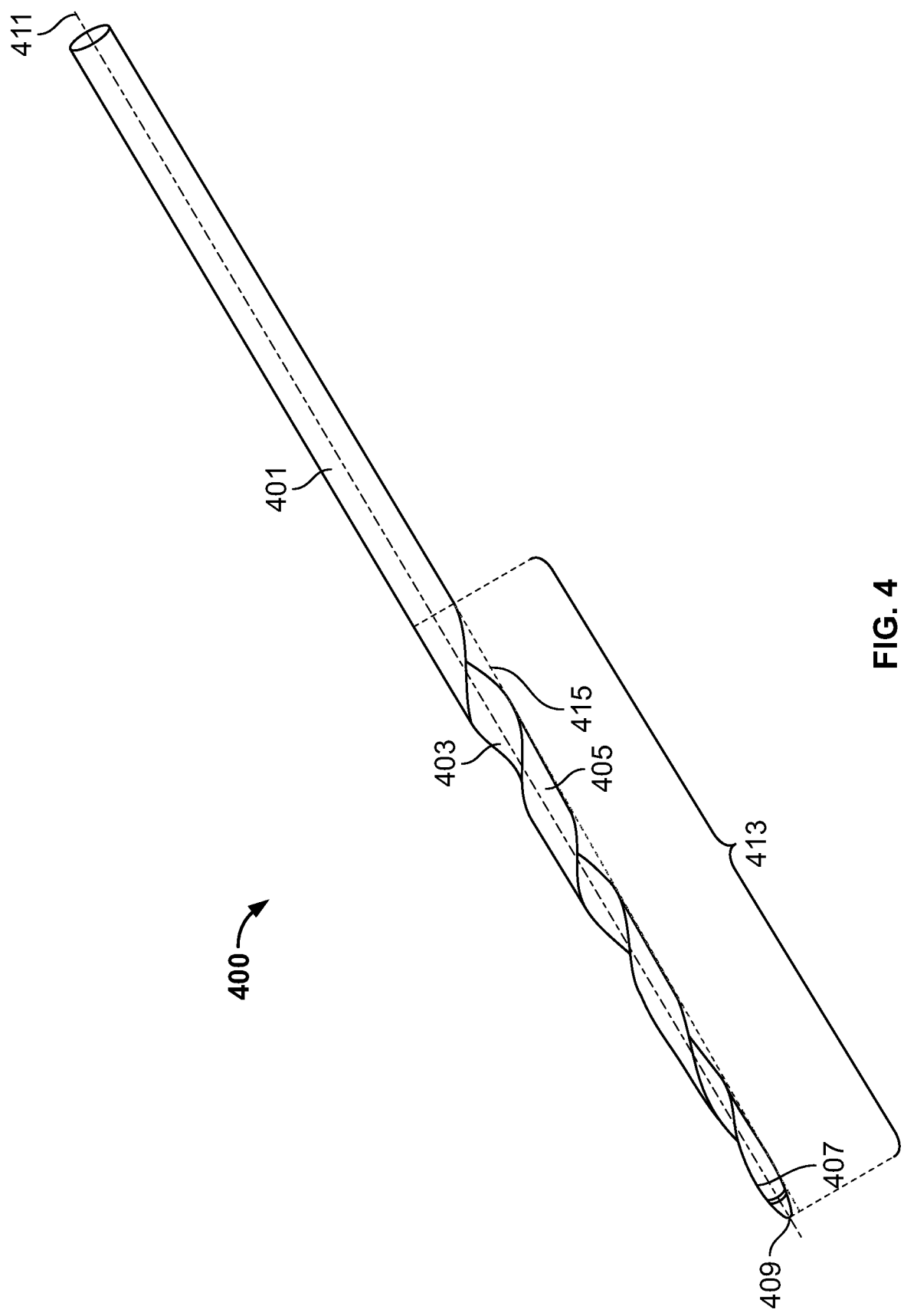
FIG. 4 shows an illustrative file in accordance with principles of the invention.

FIG. 4 shows illustrative file 400. File 400 includes shank 401. File 400 includes single flute 403, cutting edge 407 and tip 409. File 400 defines central longitudinal axis 411 and long axis 415. File 400 includes working length 413.

When operating inside a canal, flute 403 may channel capture debris dislodged by a cutting edge. Flute 403 may channel the debris from at or near the apical foramen toward the coronal area of the tooth. Flute 403 may channel debris from the tip of file 400 up toward shank 401 of file 400.

When operating inside a canal, flute 403 may additionally or alternatively capture debris. The debris may be captured inside flute 403. In exemplary methods of the invention, a practitioner may insert file 400 into a canal and advance file 400 along the canal a predetermined distance. The practitioner may subsequently remove file 400 from the canal and clean debris lodged inside flutes 403. The practitioner may then re-insert file 400 into the canal and advance file 400 further along the canal.

File 400 also includes land 405. Land 405 may be positioned between each twist or cutting edge of flute 403. Land 405 may define an outer surface (referred to alternately herein as an "outer face") of working length 413. When the working length is viewed in cross-section, one of the sides of the cross-section may correspond to the land. Land 405 may define a side of a cross-section of working length 413

Dimensions of land 405 may vary along a length working length 413. Dimensions of land 405 may remain uniform along a length of working length 413.

FIGS. 5 to 9 show illustrative symmetric cross-sections of a working length of a file in accordance with the invention. FIGS. 10 to 13 show illustrative asymmetric cross-sections of a file in accordance with the invention.

Cross-sections illustrated herein may include a reference circular perimeter. The reference circular perimeter may be used to define a percentage of solid area of a cross-section relative to a hollow area of the cross-section within the reference circular perimeter.

A file in accordance with the invention may include one or more of the cross-sections shown in FIGS. 5-13 along a length of the working length of the file. Generally, all the possible cross-section configurations disclosed herein may address specific targeted performance characteristics of a file.

Figure 5:
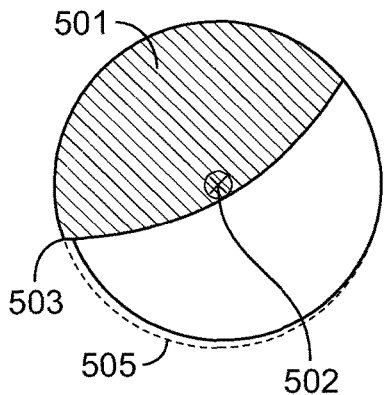
FIGS. 5-13 show illustrative cross-sections of a file in accordance with principles of the invention.

FIG. 5 shows illustrative cross-section 501 that may be utilized in a working length of a file. Cross-section 501 includes two concave sides (relative to a point within the shaded region). Cross-section 501 includes cutting edge 503. Cutting edge 503 may be used to shape a root canal when cross-section 501 is rotated about its center. FIG. 5 also shows reference circular perimeter 505 encircling the cross-sectional view. Cross-section 501 may be positioned off-center relative to central longitudinal axis 502.

FIG. 6 shows illustrative cross-section 601 that may be utilized in a working length of a file. Cross-section 601 includes a convex side and a concave side (relative to a point within the shaded region). Cross-section 601 includes cutting edge 603. Cutting edge 603 may be used to shape a root canal when cross-section 601 is rotated about its center. FIG. 6 also shows reference circular perimeter 605 encircling the cross-sectional view. Cross-section 601 may be positioned off-center relative to central longitudinal axis 607.

Figure 7:
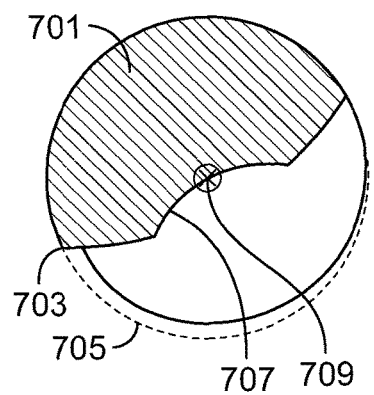

FIG. 7 shows illustrative cross-section 701 that may be utilized in a working length of a file. Cross-section 701 includes at least one convex side and at least one concave side (relative to a point within the shaded region). Cross-section 701 includes cutting edge 703. Cutting edge 703 may be used to shape a root canal when cross-section 701 is rotated about its center. FIG. 7 also shows reference circular perimeter 705 that encircles the cross-sectional view. Cross-section 701 may be positioned off-center relative to central longitudinal axis 709.

Cross-section 701 includes groove 707. Groove 707 may channel debris dislodged by cutting edge 703 through a file toward a coronal area of a tooth. Groove 707 may capture debris dislodged by cutting edge 703.

Figure 8:
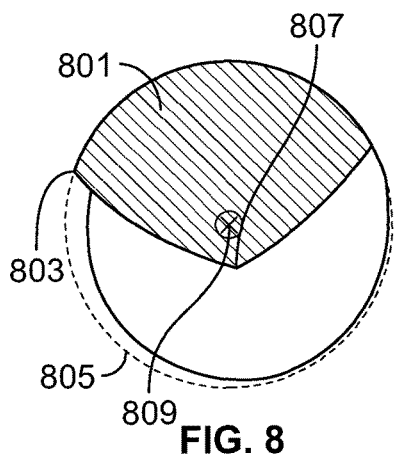

FIG. 8 shows illustrative cross-section 801 that may be utilized in a working length of a file. Cross-section 801 is symmetric, three-sided and includes three concave sides (relative to a point within the shaded region). Inner vertex 807 of cross-section 801 is positioned apart from a central longitudinal axis of a file. Thus, a working length including cross-section 801 is off-center relative to the central longitudinal axis. Cross-section 801 may be used as an alternative to existing triangular files. By being positioned off-center, a working length including cross-section 801 may provide a file with a more generous dentinal debris removal capability.

Cross-section 801 may include inner vertex 807. An inner vertex may enhance a debris removal capability of a cross-section. An inner vertex may provide added strength to a cross-section.

Cross-section 801 includes cutting edge 803. Cutting edge 803 may be used to shape a root canal when cross-section 801 is rotated about its center. FIG. 8 also shows reference circular perimeter 805 encircling the cross-sectional view. Cross-section 801 may be positioned off-center relative to central longitudinal axis 809.

Figure 9:
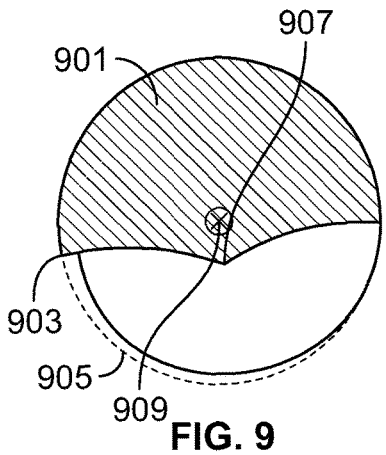

FIG. 9 shows illustrative cross-section 901 that may be utilized in a working length of a file. Cross-section 901 is symmetric, three-sided and includes two convex sides and one concave side (relative to a point within the shaded region). Cross-section 901 may include inner vertex 907. Inner vertex 907 may be positioned apart from a central longitudinal axis.

Cross-section 901 may include cutting edge 903. Cutting edge 903 may be used to shape a root canal when cross-section 901 is rotated about its center. FIG. 9 also shows reference circular perimeter 905 encircling the cross-sectional view. Cross-section 901 may be positioned off-center relative to central longitudinal axis 909.

Figure 10:
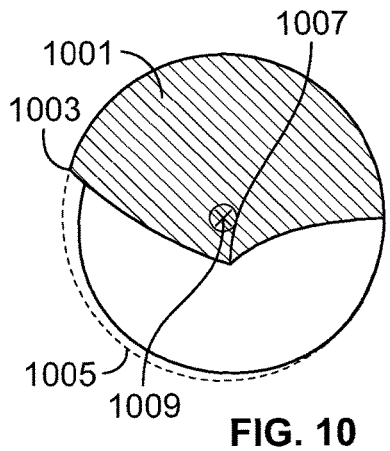

FIG. 10 shows cross-section 1001 that may be utilized in a working length of a file. Cross-section 1001 is an asymmetric, three-sided cross-section including two concave sides and one convex side (relative to a point within the shaded region). Cross-section 1001 includes inner vertex 1007. Inner vertex 1007 may be positioned apart from a central longitudinal axis.

Cross-section 1001 may include cutting edge 1003. Cutting edge 1003 may be used to shape a root canal when cross-section 1001 is rotated about its center. FIG. 10 also shows reference circular perimeter 1005 encircling the cross-sectional view. Cross-section 1001 may be positioned off-center relative to central longitudinal axis 1009.

Figure 11:
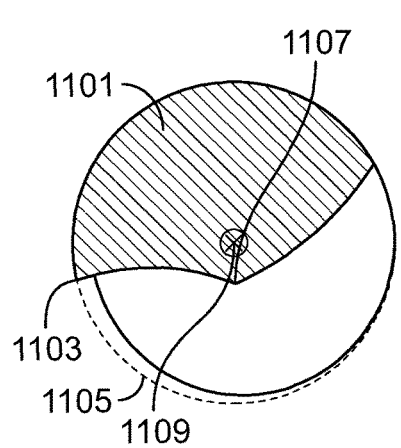

FIG. 11 shows illustrative cross-section 1101 that may be utilized in a working length of a file. Cross-section 1101 is an asymmetric, three-sided cross-section including two concave sides and one convex side (relative to relative to a point within the shaded region). Cross-section 1101 may include inner vertex 1107. Inner vertex 1107 may be positioned apart from a central longitudinal axis.

Cross-section 1101 may include cutting edge 1103. Cutting edge 1103 may be used to shape a root canal when cross-section 1101 is rotated about its center. FIG. 11 also shows reference circular perimeter 1105 that encircles the cross-sectional view. Cross-section 1101 may be positioned off-center relative to central longitudinal axis 1109.

Figure 12:
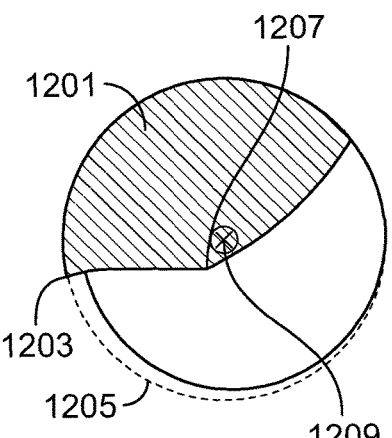

FIG. 12 shows illustrative cross-section 1201 that may be utilized in a working length of a file. Cross-section 1201 is an asymmetric, three-sided cross-section including two concave sides and one convex side (relative to a relative to a point within the shaded region). Cross-section 1201 may include inner vertex 1207. Inner vertex 1207 may be positioned apart from a central longitudinal axis.

Cross-section 1201 may include cutting edge 1203. Cutting edge 1203 may be used to shape a root canal when cross-section 1201 is rotated about its center. FIG. 12 also shows reference circular perimeter 1205 that encircles the cross-sectional view. Cross-section 1201 may be positioned off-center relative to central longitudinal axis 1209.

Figure 13:
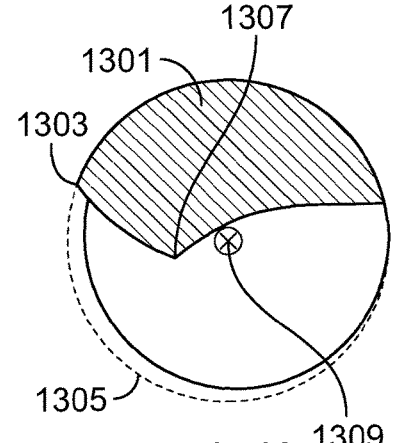

FIG. 13 shows illustrative cross-section 1301 that may be utilized in a working length of a file. Cross-section 1301 is an asymmetric, three-sided cross-section including two concave sides and a convex side (relative to a relative to a point within the shaded region).

Cross-section 1301 includes inner vertex 1307. Inner vertex 1307 may be positioned apart from a central longitudinal axis. A vertex may be an inflection point where two sides of a cross-section meet.

Cross-section 1301 may include cutting edge 1303. Cutting edge 1303 may be used to shape a root canal when cross-section 1301 is rotated about its center. FIG. 13 also shows reference circular perimeter 1305 that encircles the cross-sectional view. Cross-section 1301 may be positioned off-center relative to central longitudinal axis 1309.

Figure 14:
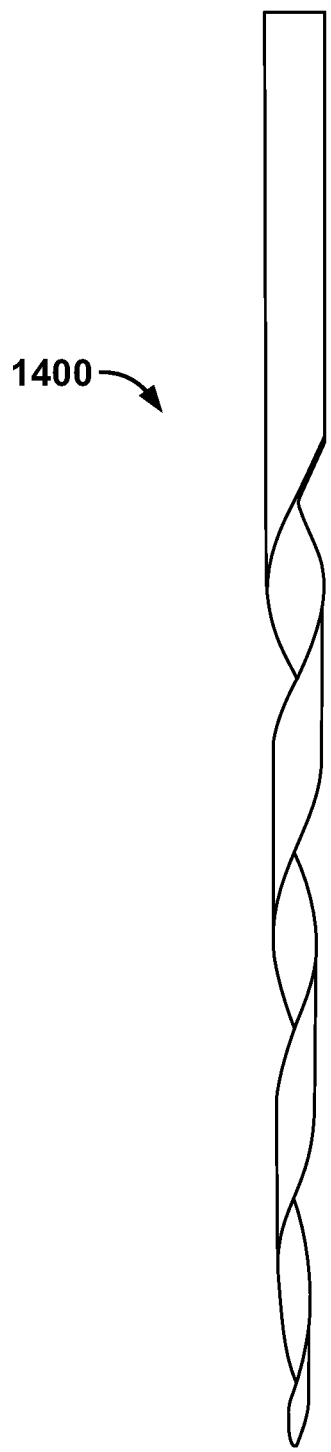
FIG. 14 shows a side view of an illustrative file in accordance with principles of the invention.

FIG. 14 shows a side view of illustrative file 1400.

Figure 15:
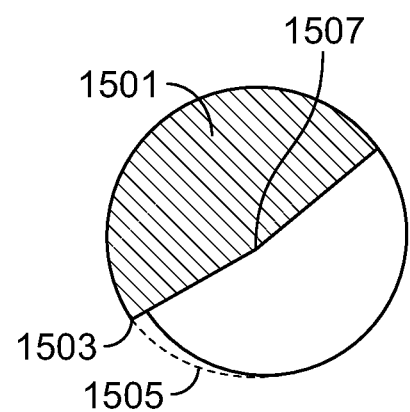
FIG. 15 shows an illustrative cross-section of a file in accordance with principles of the invention.

FIG. 15 shows an illustrative cross-sectional view of a file. A cross-section of file 1400 may substantially similar to, or identical to, the cross-section illustrated in FIG. 15. The cross-sectional view illustrated in FIG. 15 includes cross-section 1501, inner vertex 1507, cutting edge 1503 and reference circular perimeter 1505.

FIG. 16 shows a side view of illustrative file 1600.

Figure 17A:
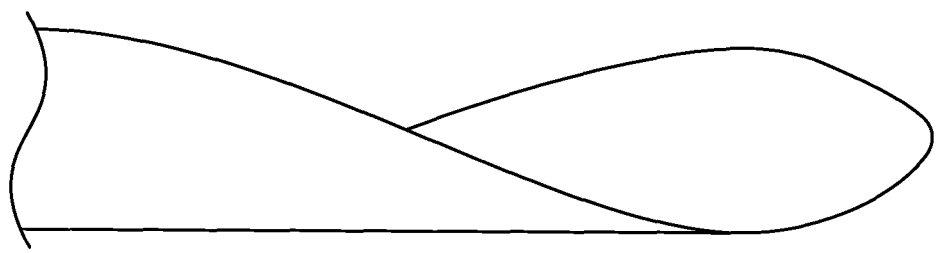
FIGS. 17A and 17B show an enlarged view of apparatus shown in FIG. 16.
Figure 17B:
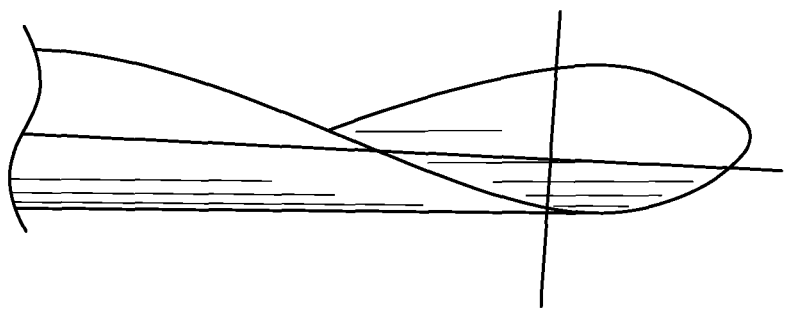

FIGS. 17A and 17B show detail of illustrative tip region 1700 of file 1600. Tip region 1700 includes a "spoon-shaped" tip. A "spoon-shaped" tip may enhance the cutting efficiency of file 1600.

Figure 18:
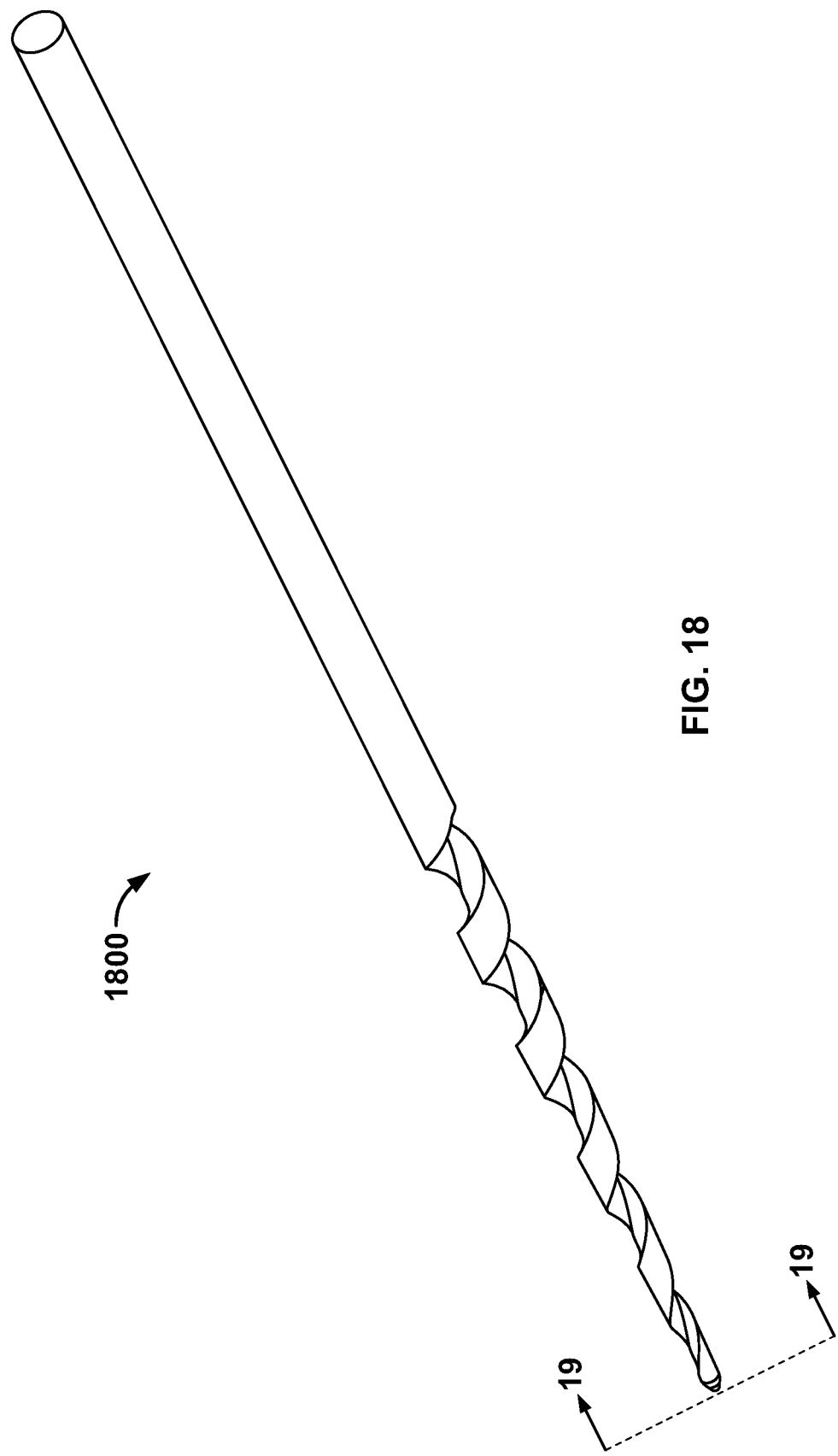
FIG. 18 shows a perspective view of an illustrative file in accordance with principles of the invention.

FIG. 18 shows a perspective view of illustrative file 1800.

Figure 19:
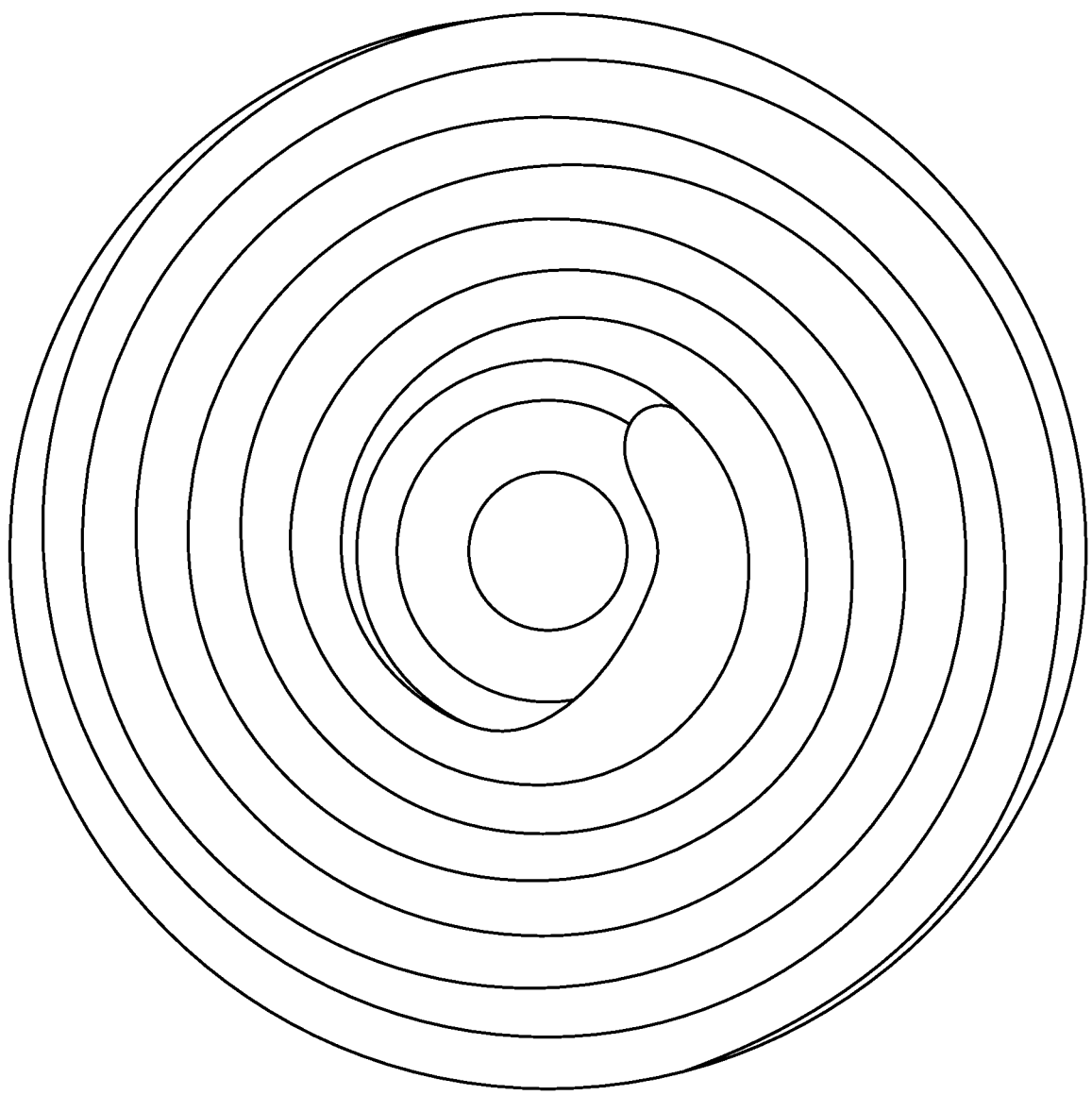
FIG. 19 shows a view of FIG. 18 taken along lines 19-19.

FIG. 19 shows a view of file 1800 taken along lines 19-19 (shown in FIG. 18). FIG. 19 shows that file 1800 may include cross-sections of varying diameter. Varying the diameter may give file 1800 a tapered shape. The tapered shape may allow file 1800 to maintain an anatomical shape of the canal when operating in the canal. FIG. 19 also shows that file 1800 may include a core taper of varying diameter. In some embodiments, a file core may be hollow.

Figure 20A:
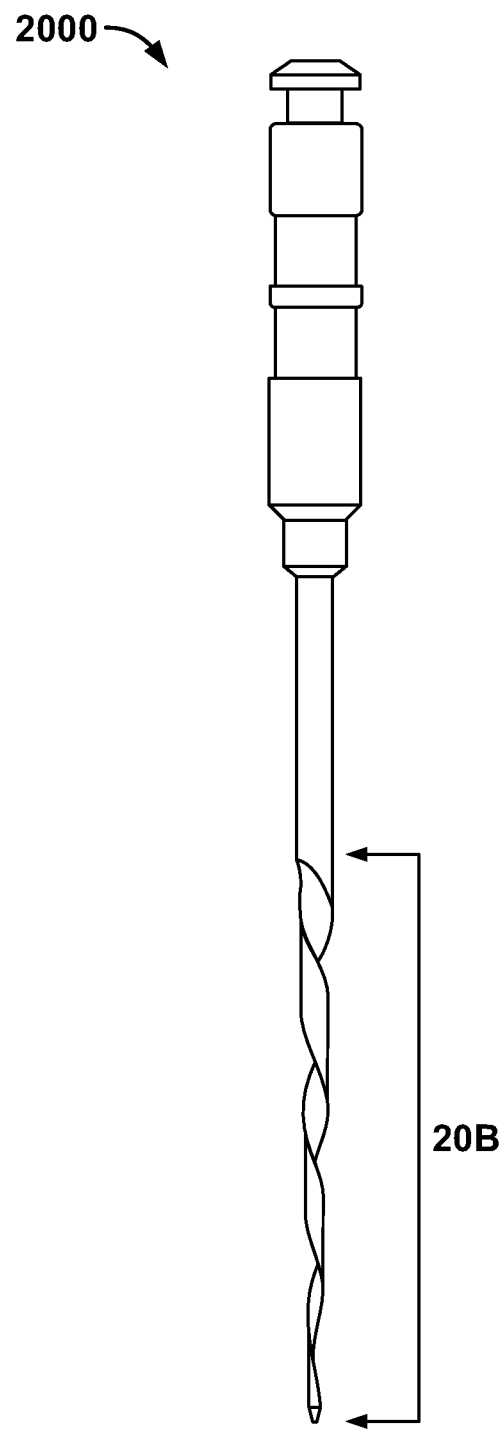
FIG. 20A shows an illustrative file in accordance with principles of the invention.

FIG. 20A shows, illustrative file 2000.

Figure 20B:
FIG. 20B shows a view of apparatus shown in FIG. 20A taken along lines 20B-20B.

FIG. 20B shows a view of file 2000 taken along lines 20B-20B (shown in FIG. 20A).

Figure 21A:
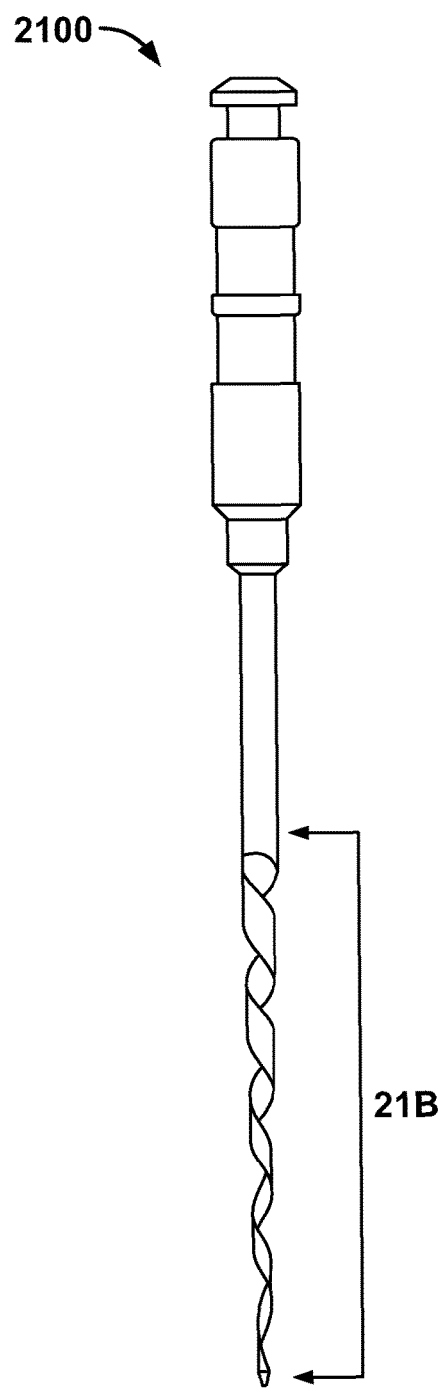
FIG. 21A shows an illustrative file in accordance with principles of the invention.

FIG. 21A shows illustrative file 2100.

Figure 21B:
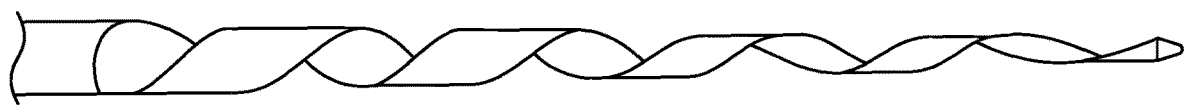
FIG. 21B shows a view of apparatus shown in FIG. 21A taken along lines 21B-21B.

FIG. 21B shows a view of file 2100 taken along lines 21B-21B (shown in FIG. 21A). FIG. 21B shows that, along lines 21B-21B, file 2100 includes variable spacing between each twist of the flute.

The land of file 2000 is longer than the land of file 2100. The flute of file 2100 includes more helical twists than the flute of file 2000.

A number of helical twists and/or pitch of a flute may provide different RAC values. A number of helical twists, depth and/or pitch of a flute may provide different flexibilities of the file at different points along a length of a file.

FIG. 22 shows illustrative file 2200.

FIG. 23 shows cross-section 2300 of file 2200 taken along cut lines 23-23 (shown in FIG. 22).

FIG. 24 shows cross-section 2401 of file 2200 taken along cut lines 24-24 (shown in FIG. 22). FIG. 24 also shows reference circular perimeter 2403. Cross-section 2401 may include four straight sides and a concave side (relative to a point within the shaded region). In some embodiments, a working length of file 2200 may instead have a cross-section defining one or more convex sides (relative to a point within the shaded region).

Figure 25:
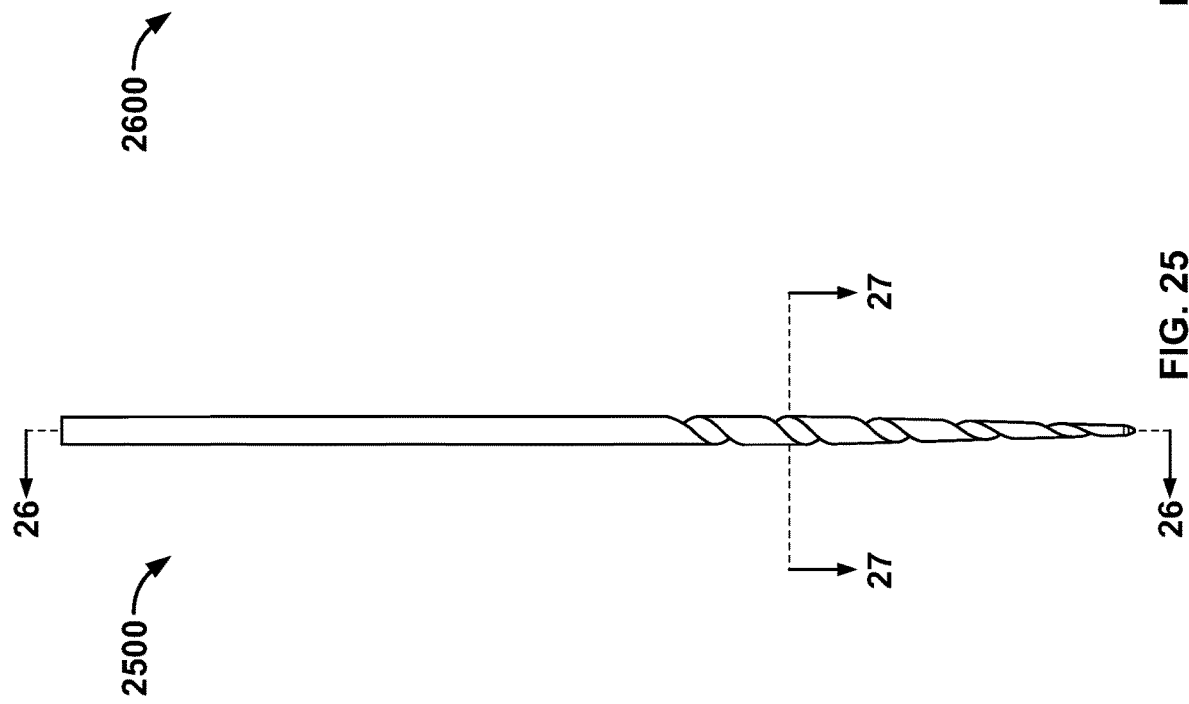
FIG. 25 shows an illustrative file in accordance with principles of the invention.

FIG. 25 shows illustrative file 2500.

Figure 26:
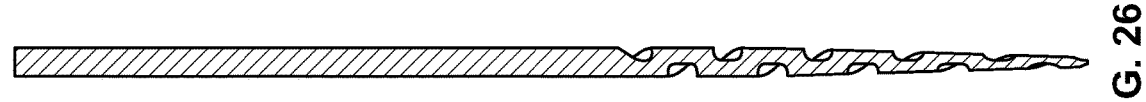
FIG. 26 shows a cross-sectional view of FIG. 25 taken along lines 26-26.

FIG. 26 shows cross-section 2600 of file 2500 taken along cut lines 26-26 (shown in FIG. 25).

Figure 27:
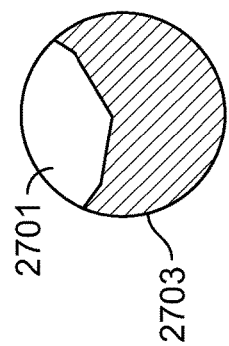
FIG. 27 shows a cross-sectional view of FIG. 25 taken along lines 27-27.

FIG. 27 shows cross-section 2701 of file 2500 taken along cut lines 27-27 (shown in FIG. 25). Cross-section 2701 is a symmetrical cross-section. Cross-section 2701 may include four straight sides forming a convex profile (relative to a point within the shaded region). Cross-section 2701 also includes a concave side. In some embodiments, a working length of file 2500 may instead have sides defining one or more convex sides, one or more concave side and/or one or more concave profiles. FIG. 27 also shows reference circular perimeter 2703.

Figure 28:
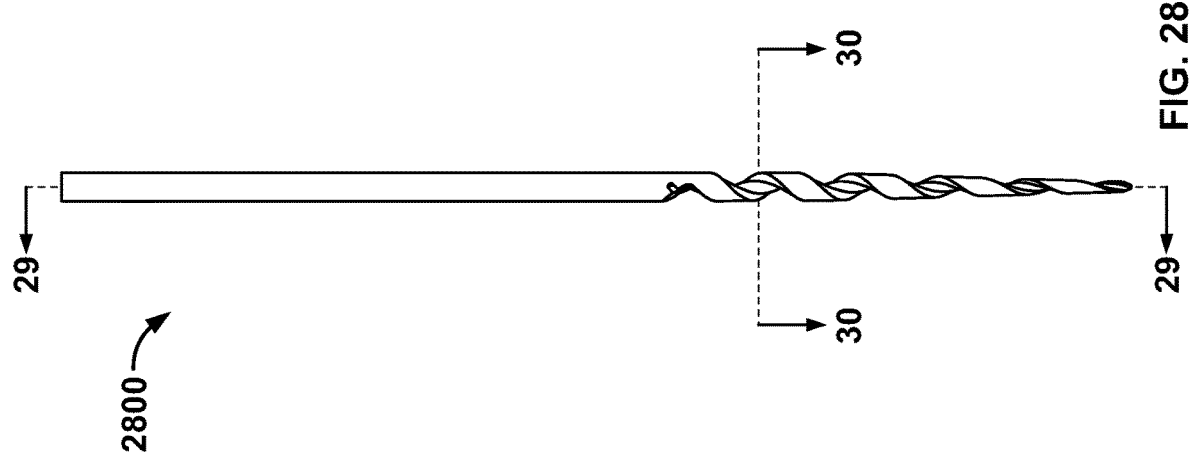
FIG. 28 shows an illustrative file in accordance with principles of the invention.

FIG. 28 shows illustrative file 2800.

Figure 29:
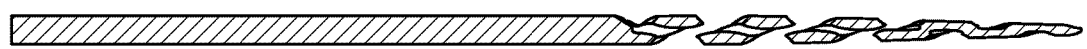
FIG. 29 shows a cross-sectional view of FIG. 28 taken along lines 29-29.

FIG. 29 shows cross-section 2900 of file 2800 taken along cut lines 29-29 (shown in FIG. 28). Cross-section 2900 shows that file 2800 includes less material than file 2200 and file 2500.

Figure 30:
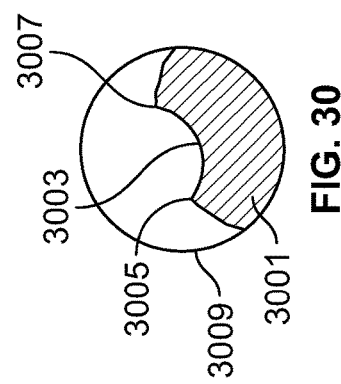
FIG. 30 shows a cross-sectional view of FIG. 28 taken along lines 30-30.

FIG. 30 shows cross-section 3001 of file 2800 taken along cut line 30-30 (shown in FIG. 28). Cross-section 3001 is a symmetrical cross-section. FIG. 30 also shows reference circular perimeter 3009.

Cross-section 3001 includes a convex side and a concave side (relative to a point within the shaded region). Cross-section 3001 also includes straight sides forming concave profiles. The convex side between inner vertices 3005 and 3007 may define groove 3003. Groove 3003 may run along some or all of a working length of file 2800.

FIG. 31 shows illustrative file 3110.

FIG. 32 shows cross-section 3200 of file 3110 taken along cut lines 32-32 (shown in FIG. 31).

FIG. 33 show cross-section 3301 of file 3110 taken along cut lines 33-33 (shown in FIG. 31). Cross-section 3301 may include a concave (relative to a point within the shaded region) profile defined by straight sides. In some embodiments, a working length of file 3100 may include a cross-section that includes a convex (relative to a point within the shaded region) side and/or one or more sides defining a convex profile.

Cross-section 3301 may include vertices. An exemplary vertex is inner vertex 3303. FIG. 33 also shows reference circular perimeter 3305.

FIG. 34 shows an illustrative file 3400.

FIG. 35 shows cross-section 3500 of file 3400 taken along cut lines 35-35 (shown in FIG. 34).

FIG. 36 shows cross-section 3601 of file 3400 taken along cut lines 36-36 (shown in FIG. 34). Cross-section 3601 includes straight sides that define a convex (relative to a point within the shaded region) profile. Cross-section 3601 includes straight sides that define a concave (relative to a point within the shaded region) profile. Cross-section 3601 includes a concave side (relative to a point within the shaded region). In some embodiments, a working length of file 3400 may include a cross-section defining any suitable number of straight sides, convex and/or concave sides.

Cross-section 3601 may include a plurality of inner vertices, such as inner vertex 3603. Cross-section 3601 has a larger perimeter than cross-section 3301. FIG. 36 also shows reference circular perimeter 3605.

FIG. 37 shows illustrative file 3700.

FIG. 38 shows cross-section 3800 of file 3700 taken along cut lines 38-38 (shown in FIG. 37).

FIG. 39 shows cross-section 3901 of file 3700 taken along cut lines 39-39 (show in FIG. 37). Cross-section 3901 is an asymmetrical cross-section. Cross-section 3901 includes straight sides that define one or more inner vertices and a concave profile (relative to a point within the shaded region). Cross-section 3901 also includes straight sides that define a convex profile (relative to a point within the shaded region).

Cross-section 3901 may include a plurality of inner vertices, such as inner vertex 3903. FIG. 39 also shows reference circular perimeter 3905.

FIG. 40 shows illustrative file 4000.

FIG. 41 shows cross-section 4100 of file 4000 taken along cut lines 41-41 (shown in FIG. 40).

FIG. 42 shows cross-section 4201 of file 4000 taken along cut lines 42-42 (shown in FIG. 40). Cross-section 4201 is an asymmetrical cross-section. Cross-section 4201 includes straight sides that define a convex profile (relative to a point within the shaded region). Cross-section 4201 also includes straight sides that define a concave profile (relative to a point within the shaded region). In some embodiments, a working length of file 4000 may include a cross-section that includes any suitable number straight, convex and/or concave sides.

Cross-section 4201 may include a plurality of inner vertices, such as inner vertex 4203. FIG. 42 also shows reference circular perimeter 4205.

Figure 43:
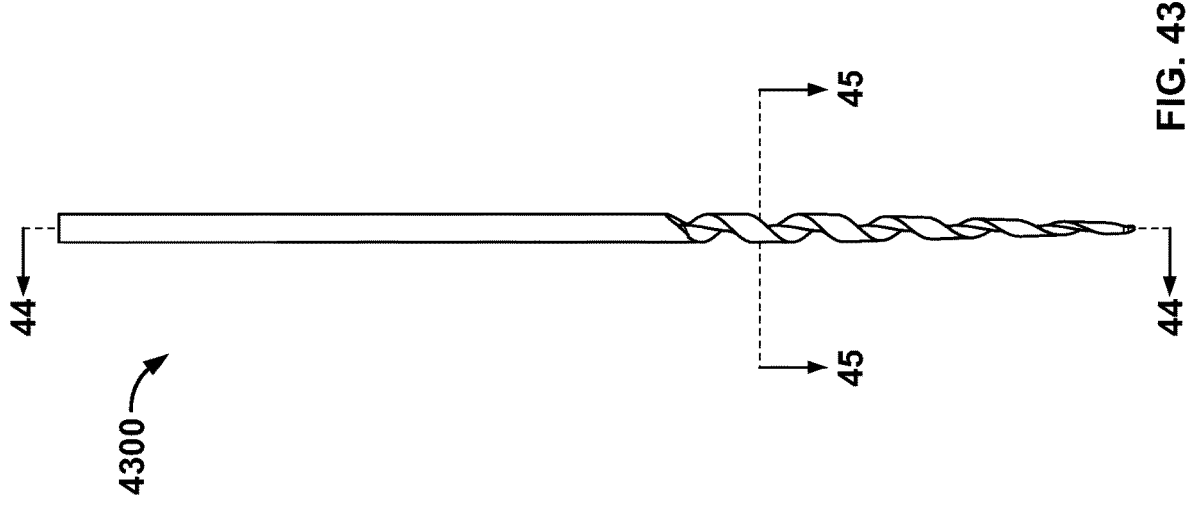
FIG. 43 shows an illustrative file in accordance with principles of the invention.

FIG. 43 shows illustrative file 4300.

Figure 44:
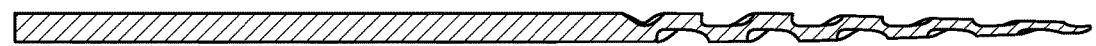
FIG. 44 shows a cross-sectional view of FIG. 43 taken along lines 44-44.

FIG. 44 shows cross-section 4400 of file 4300 taken along cut lines 44-44 (shown in FIG. 43).

Figure 45:
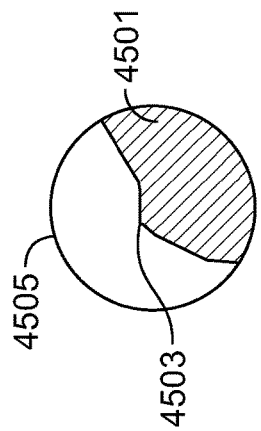
FIG. 45 shows a cross-sectional view of FIG. 43 taken along lines 45-45.

FIG. 45 shows cross-section 4501 of file 4300 taken along cut lines 45-45 (shown in FIG. 43). Cross-section 4501 may be asymmetric. Cross-section 4501 may include four straight sides and a concave side (relative to a point within the shaded region). In some embodiments, a working length of file 4300 may include a cross-section defining any suitable number of straight, convex and/or concave sides.

Cross-section 4501 may include a plurality of inner vertices, such as inner vertex 4503. FIG. 45 also shows reference circular perimeter 4505.

FIG. 46 shows illustrative file 4600.

FIG. 47 shows cross-section 4700 of file 4600 taken along cut lines 47-47 (shown in FIG. 46).

FIG. 48 show cross-section 4801 of file 4600 taken along cut lines 48-48 (shown in FIG. 46). Cross-section 4801 may be asymmetric. Cross-section 4801 includes four straight sides and a concave side (relative to a point within the shaded region). In some embodiments, a working length of file 4600 may include a cross-section defining any suitable number of straight, concave and/or convex sides.

Cross-section 4801 may include inner vertex 4807, inner vertex 4805 and inner vertex 4803. FIG. 48 also shows reference circular perimeter 4809.

Figure 49:
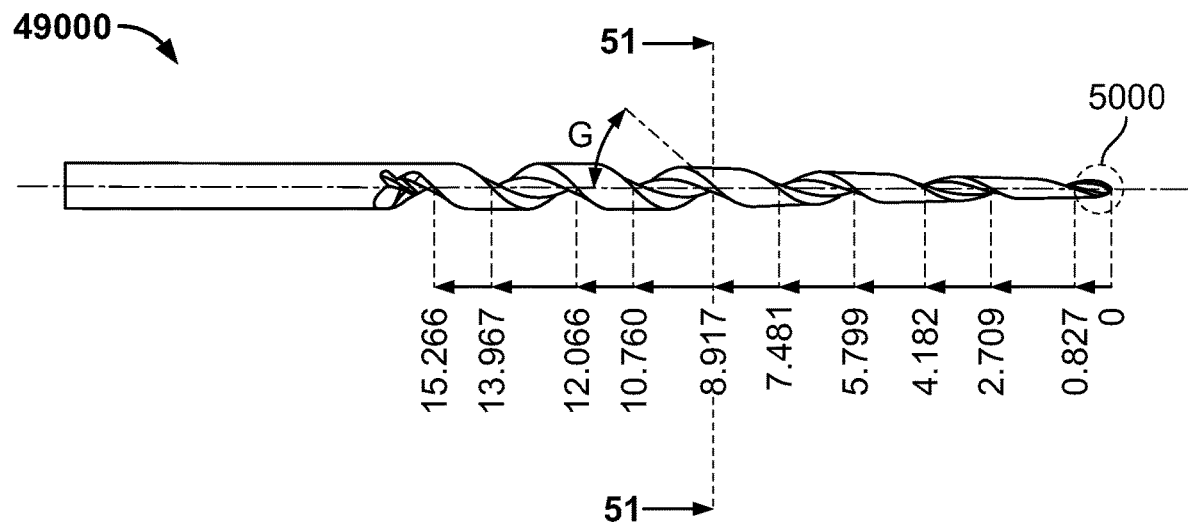
FIG. 49 shows an illustrative file in accordance with principles of the invention.

FIG. 49 shows illustrative file 4900 and associated dimensions of file 4900. File 4900 has a variable pitch along the length of file 4900.

Figure 50:
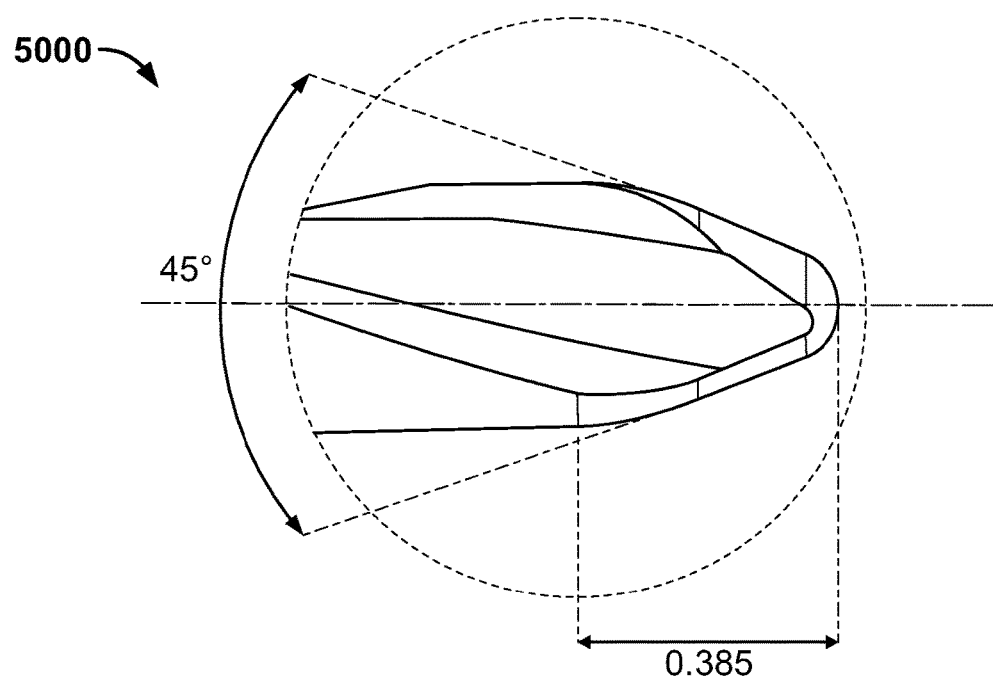
FIG. 50 shows an enlarged view of a portion of apparatus shown in FIG. 49.

FIG. 50 shows an enlarged view of tip region 5000 of file 4900. Tip region 5000 includes a tip. The tip may be "spoon-shaped." The tip may be fluted.

Figures 51, 52:
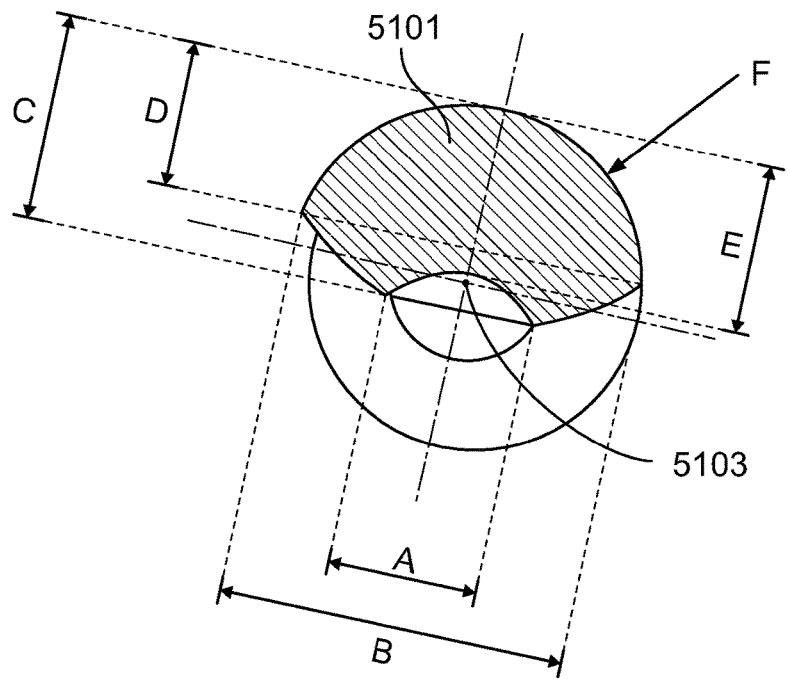
FIG. 51 shows a cross-sectional view of FIG. 49 taken along lines 51-51.
FIG. 52 shows illustrative measurements of portions of apparatus shown in FIG. 49.

FIG. 51 shows cross-section 5100 of file 4900 taken along cut lines 51-51 (shown in FIG. 50).

FIG. 52 shows the measurements of sections A, B, C, D, E and F of cross-sections of file 4900. The measurements of actions A, B, C, D, E and F are taken perpendicular to a central axis of file 490 and at positions defined in FIG. 49.

FIG. 53 shows blank 5301 that may be used to form file 5303 using any of the manufacturing methods disclosed herein, such as grinding, twisting and EDM.

FIGS. 54-93 show exemplary embodiments of cross-sectional geometries of a working length of a file in accordance with the invention.

FIGS. 54-60 show illustrative cross-sections that may be used to construct a working length of a file in accordance with the invention. The cross-sections are shown within an illustrative reference circle. The reference circle shown in FIGS. 54-60 may show a cross-section of a blank used to manufacture the file prior to being cut to size. The cross-section within the circle may show the cross-section of the blank after the manufacturing process is completed.

A working length of a file in accordance with the invention may include one or more of the cross-sections shown in FIGS. 54-93. Generally, all the possible cross-section configurations disclosed herein may address specific targeted performance characteristics of a file.

FIGS. 61-93 show illustrative cross-sections of files in accordance with the invention within reference circular perimeters. A working length of a file in accordance with the invention may include one or more of the cross-sections shown in FIGS. 61-93. Generally, all the possible cross-section configurations disclosed herein may address specific targeted performance characteristics of a file. Illustrative performance characteristics may include debris removal, cutting efficiency, file strength, file flexibility or any suitable performance characteristic.

Some of the geometries show in FIGS. 54-93 include scalloped shapes on their inside surfaces. The scalloped shapes may encourage irrigating solution to course down the file during cutting to wash cut debris out.

Some of the geometries show in FIGS. 54-93 are designed to require fewer grinding wheel cuts during manufacture, if the geometries are manufactured using a grinding process. This is advantageous at least because it increases the manufacturing speed, since each different surface on the file may require another grinding pass.

FIG. 54 shows a triangular cross-section.

FIG. 55 shows a three-sided cross-section that includes three curved sides.

FIG. 56 shows a two-sided cross-section that includes a curved side and a straight side.

FIG. 57 shows an off-center, asymmetric, tear-drop shaped cross-section.

FIG. 58 shows an off-center, asymmetric, grooved, tear-drop shaped cross-section.

FIG. 59 shows an off-center, asymmetric, tear-drop shaped cross-section.

FIG. 60 shows an off-center, four-sided cross-section. In FIG. 60, two of the sides are curved and two of the sides are straight.

Figure 61:
FIGS. 61-93 show illustrative cross-sections of a file in accordance with the principles of the invention.

FIG. 61 shows a diamond-shaped, off-center cross-section having curved sides. FIG. 61 is also a four-sided cross section. In other embodiments, a diamond-shaped cross-section may include straight sides or a combination of straight and curved sides.

Figure 62:

FIG. 62 shows an off-center, asymmetrically shaped four-sided cross-section. FIG. 62 includes an inner vertex.

Figure 63:

FIG. 63 shows a triangular, off-center, three-sided cross-section that includes an inner vertex.

Figure 64:

FIG. 64 shows a triangular, off-center, three-sided cross-section that includes an inner vertex.

Figure 65:

FIG. 65 shows an off-center, diamond-shaped cross-section that includes curved and straight sides. The cross-section shown in FIG. 65 includes three outer vertices and one inner vertex.

Figure 66:
Figure 67:

FIG. 66 shows an off-center, asymmetric, four-sided cross-section.

Figure 68:

FIG. 68 shows an off-center cross-section that includes two inner vertices. The cross-section of FIG. 68 also includes four curved sides.

Figure 69:

FIG. 69 shows an off-center, four-sided cross section. The cross-section of FIG. 69 includes three straight sides, one curved side and an inner vertex.

Figure 70:

FIG. 70 shows an off-center, three-sided cross-section that includes an inner vertex.

Figure 71:

FIG. 71 shows an off-center, asymmetric, four-sided cross-section that includes an inner vertex.

Figure 72:

FIG. 72 shows an off-center, three-sided cross-section.

Figure 73:

FIG. 73 shows an off-center, three-sided cross-section that includes two straight sides and one curved side.

Figure 74:

FIG. 74 shows an off-center, crescent shaped, two-sided cross-section.

Figure 75:

FIG. 75 shows an off-center, three-sided cross-section with three outer vertices. The cross-section of FIG. 75 includes two curved sides and one straight side.

Figure 76:

FIG. 76 shows an off-center, crescent shaped, two-sided cross-section.

Figure 77:

FIG. 77 shows an off-center, three-sided cross section that includes two straight sides and one curved side.

Figure 78:

FIG. 78 shows an off-center, two-sided cross section that includes one straight side and one curved side.

Figure 79:

FIG. 79 shows an off-center, triangular shaped cross-section.

Figure 80:

FIG. 80 shows an off-center, three-sided cross-section having three outer vertices.

Figure 81:

FIG. 81 shows an off-center, tear-drop shaped cross-section that includes an outer vertex.

Figure 82:

FIG. 82 shows an off-center, tear-drop shaped cross-section that includes one outer vertex.

Figure 83:

FIG. 83 shows an off-center, triangular shaped cross-section. Two sides of the cross section shown in FIG. 83 may meet (i.e. form a vertex) at a 90-degree angle.

Figure 84:

FIG. 84 shows an off-center, asymmetric, four-sided cross-section that includes two inner vertices.

Figure 85:

FIG. 85 shows an off-center, asymmetric five-sided cross-section.

Figure 86:

FIG. 86 shows an off-center, tear-drop shaped and grooved cross-section.

Figure 87:

FIG. 87 shows an off-center, tear-drop shaped and grooved cross-section.

Figure 88:

FIG. 88 shows an off-center, rainbow-shaped four-sided cross section. A side may be a portion of a cross-section that extends between two vertices.

Figure 89:

FIG. 89 shows an off-center, rainbow-shaped four-sided cross-section.

Figure 90:

FIG. 90 shows an off-center, four-sided cross section.

Figure 91:

FIG. 91 shows an off-center, five-sided cross section.

Figure 92:

FIG. 92 shows an off-center, five-sided cross section.

Figure 93:

FIG. 93 shows an off-center, rainbow-shaped, four-sided cross section.

Figure 94:
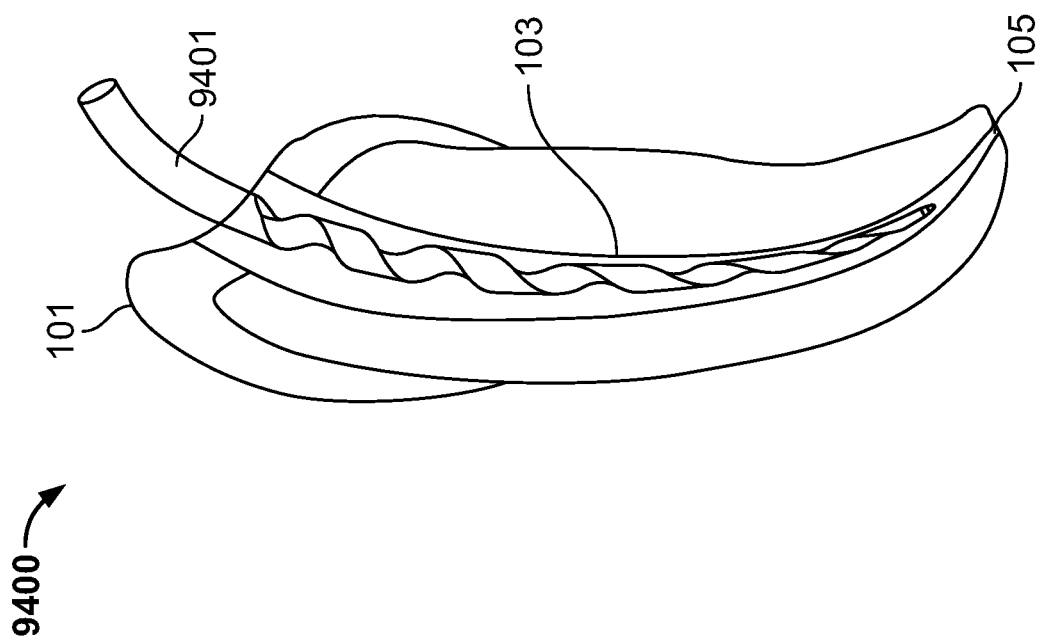
FIG. 94 shows an illustrative file in accordance with principles of the invention inserted into a tooth during an endodontic procedure.

FIG. 94 shows illustrative view 9400 of file 9401 inserted into a tooth during an endodontic procedure. View 9400 may illustrate file 9401 prior to rotation of file 9401 by an endodontic practitioner.

Figure 95:
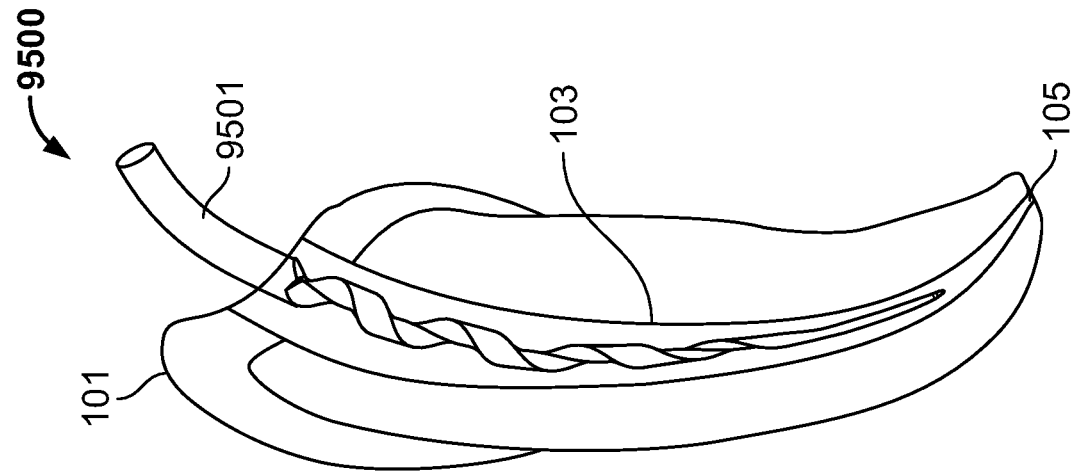
FIG. 95 shows an illustrative file in accordance with principles of the invention inserted into a tooth during an endodontic procedure.

FIG. 95 shows illustrative view 9500 of file 9501 inserted into a tooth during an endodontic procedure. View 9500 may illustrate file 9501 after rotation of file 9401 by a practitioner. The practitioner may rotate file 9501 by hand or machine. View 9500 illustrates the deformation and stretching of file 9501 resulting from file 9401's rotation.

Figure 96:
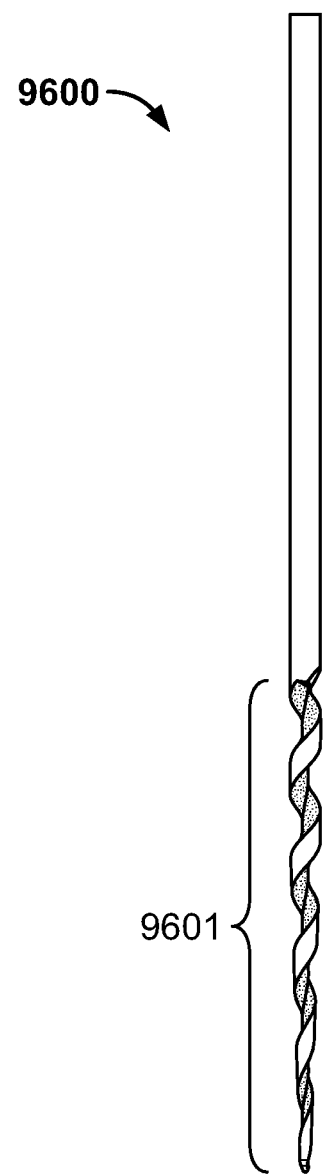
FIG. 96 shows an illustrative file in accordance with principles of the invention after capturing tissue within a tooth.

FIG. 96 shows illustrative file 9600. File 9600 may have been rotated in a tooth during an endodontic procedure and subsequently removed. File 9600 may include working length 9601. Working length 9601 includes a single flute. The singe flute of working length 9601 is full of tissue removed from the tooth during the endodontic procedure.

The single flute design of file 9600 may contribute to enhanced debris removal properties of file 9600 in comparison to a prior-art file. The off-center design of file 9600 may contribute to enhanced debris removal properties of file 9600 in comparison to a prior-art file.

Figure 97:
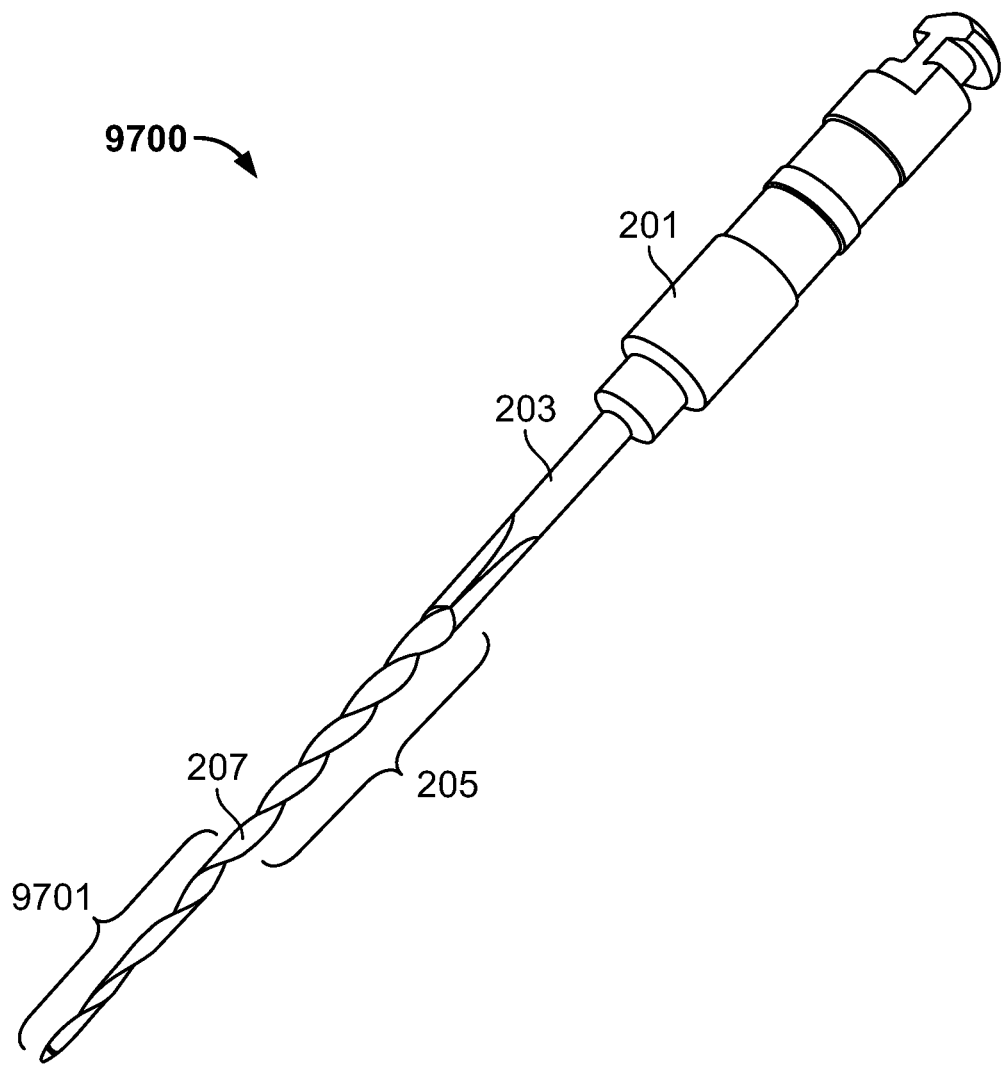
FIG. 97 shows an illustrative file in accordance with principles of the invention.

FIG. 97 shows illustrative file 9700. A working length of file 9700 may include first length 205 and second length 9701. First length 205 may include two flutes. Second length 9701 may include a single flute. First length 205 may give file 9700 enhanced strength. Second length 9701 may give file 9700 enhanced flexibility and debris removal capabilities.

Figure 98:
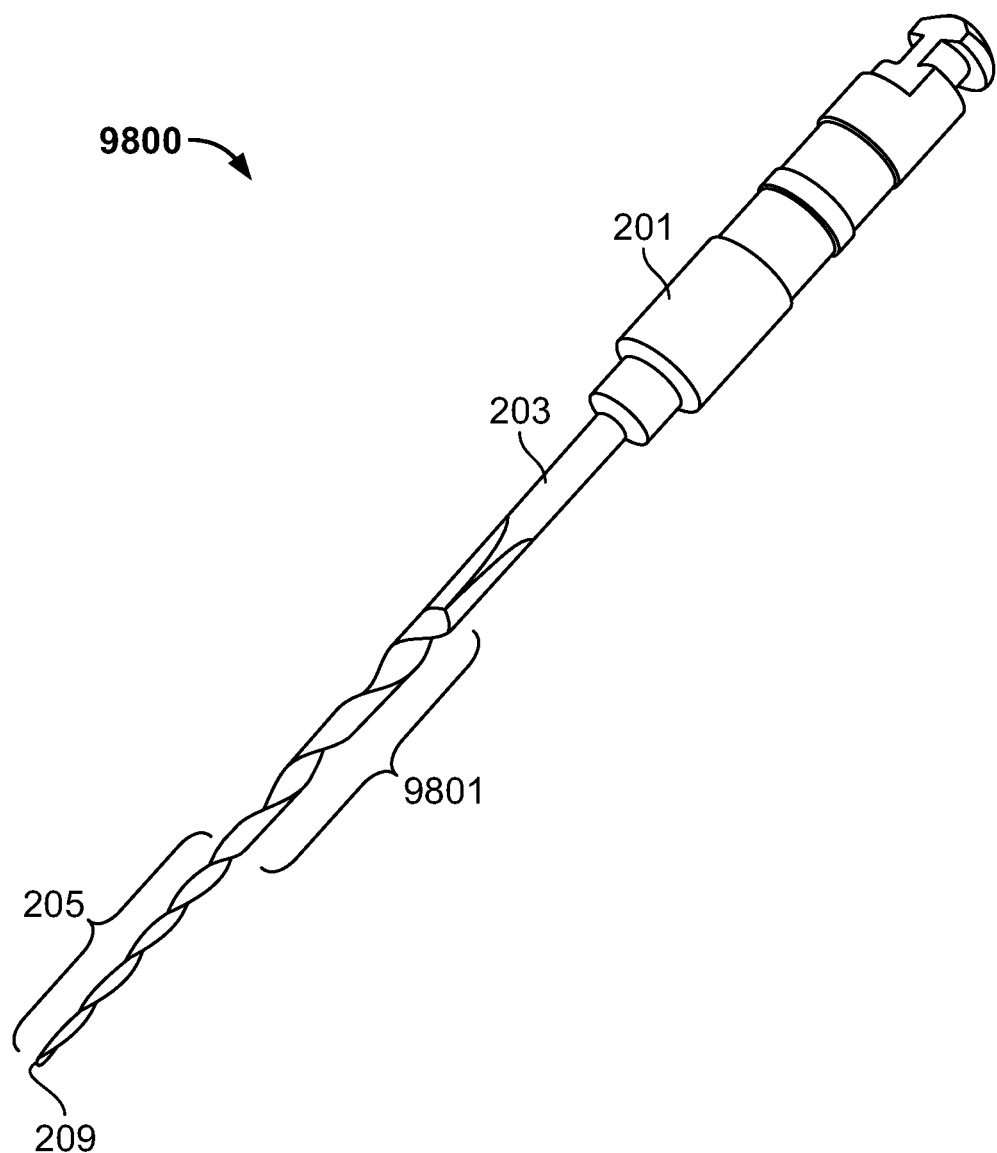
FIG. 98 shows an illustrative file in accordance with principles of the invention.

FIG. 98 shows illustrative file 9800. A working length of file 9800 may include first length 9801 and second length 205. First length 9801 may include a single flute. Second length 205 may include two flutes. First length 9801 may give file 9800 enhanced flexibility and debris removal capabilities. Second length 205 may give file 9800 enhanced strength.

Figure 99:
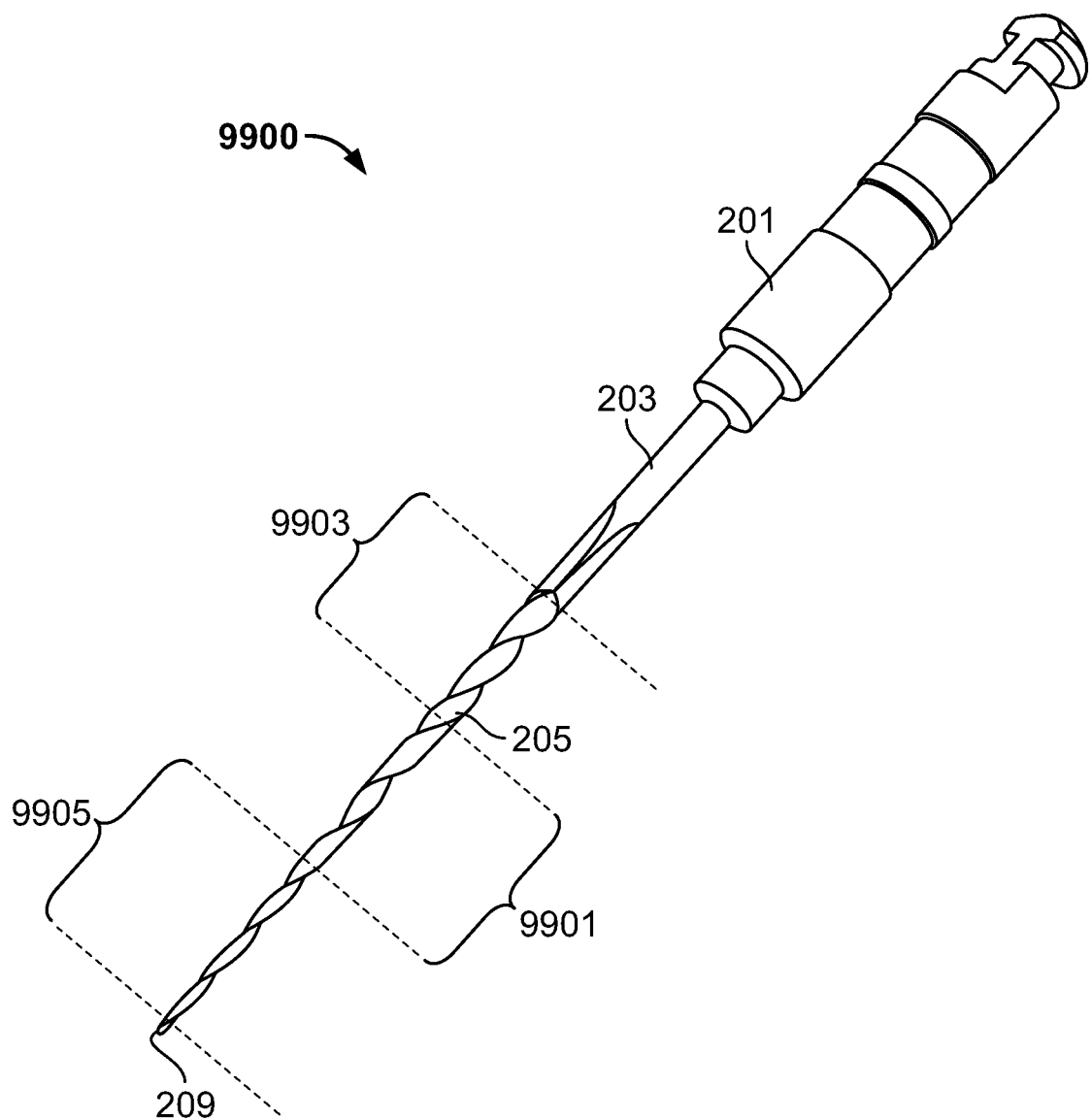
FIG. 99 shows an illustrative file in accordance with principles of the invention.

FIG. 99 shows illustrative file 9900. A working length of file 9900 may include length 9903, length 9901 and length 9905. Length 9903 and length 9905 may both include two flutes. Length 9901 may include one flute. Length 9903 and length 9905 may both give file 9900 enhanced strength. Length 9901 may give file 9900 enhanced flexibility and debris removal characteristics.

Thus, apparatus and methods for a fluted endodontic file have been provided. Persons skilled in the art will appreciate that the present invention can be practiced by other than the described examples, which are presented for purposes of illustration rather than of limitation. The present invention is limited only by the claims that follow.

What is claimed is:

1. A fluted endodontic file defining a central longitudinal axis and including a working length extending along the central longitudinal axis, wherein:
the working length includes a single flute extending along the central longitudinal axis; and
the working length defines an off-center cross-section along the central longitudinal axis, the cross-section including three vertices that define a triangular region; wherein:
the single flute comprises a cutting edge configured to cut tooth tissue;
the cross section defines a first side, a second side and a third side; and
the first side, the second side and the third side are each concave relative to a point within the cross-section.

2. The fluted endodontic file of claim 1 wherein one of the three vertices is an inner vertex positioned apart from the central longitudinal axis.

3. The fluted endodontic file of claim 1 wherein:
the working length defines a plurality of off-center cross-sections along the central longitudinal axis, the plurality of off-center cross-sections including the cross-section; and
distances between an inner vertex of each of the plurality of off-center cross-sections and the central longitudinal axis are constant along the working length.

4. The fluted endodontic file of claim 1 wherein:
the working length defines a plurality of off-center cross-sections along the central longitudinal axis, the plurality of off-center cross-sections including the cross-section; and
distances between an inner vertex of each the plurality of off-center cross-sections and the central longitudinal axis vary along the working length.

5. The fluted endodontic file of claim 1 further comprising a spoon-shaped tip positioned at an end of the working length and being configured to cut tooth tissue.

6. The fluted endodontic file of claim 5 wherein the spoon-shaped tip has a half conical shape with a concave radius and includes a tip cutting edge extending along a side of the tip.

7. The endodontic file of claim 1 wherein the cross-section defines an area that does not include the central longitudinal axis.

8. The endodontic file of claim 1 wherein the cross-section defines an area that includes the central longitudinal axis.

9. The fluted endodontic file of claim 1 wherein the cross-section comprises an area of 20 to 75% of a total area circumscribed by a circle surrounding the cross-section.

10. The fluted endodontic file of claim 1 wherein:
the working length includes a first portion extending along the central longitudinal axis and a second portion adjacent the first portion and extending along the central longitudinal axis;
the working length defines a first plurality of cross-sections along the first portion, the first plurality of cross-sections including the cross-section and having three vertices; and
the working length defines a second plurality of cross-sections along the second portion, the second plurality of cross-sections having two vertices.

11. A fluted endodontic file defining a central longitudinal axis and including a working length extending along the central longitudinal axis, wherein:
the working length includes:
a single flute;
a first portion extending along the central longitudinal axis; and
a second portion adjacent the first portion and extending along the central longitudinal axis;
the working length defines a first plurality of cross-sections having a first number of sides along the first portion; and
the working length defines a second plurality of cross-sections having a second number of sides along the second portion.

12. The fluted endodontic file of claim 11 wherein:
the first plurality of cross-sections has three sides; and
the second plurality of cross-sections has two sides.

13. The fluted endodontic file of claim 11 wherein:
each of the first plurality of cross-sections define at least one convex side relative to a point within the corresponding cross-section; and
each of the second plurality of cross-sections define at least one concave side relative to a point within the corresponding cross-section.

14. The endodontic file of claim 11 wherein:
the single flute extends along the first portion; and
the working length includes two flutes extending along the second portion; and
the first portion extends away from a shank of the file; and
the second portion includes a tip of the file.

15. The endodontic file of claim 14 wherein the first portion comprises two-thirds of the working length and the second portion comprises one-third of the working length.

16. The endodontic file of claim 11 wherein the single flute passes through a tip region of the file.

* * * * *